(12) United States Patent
Kimoto et al.

(10) Patent No.: US 9,050,054 B2
(45) Date of Patent: Jun. 9, 2015

(54) MEDICAL IMAGE DIAGNOSTIC APPARATUS

(71) Applicants: Kabushiki Kaisha Toshiba, Tokyo (JP); Toshiba Medical Systems Corporation, Otawara-shi (JP)

(72) Inventors: Tatsuya Kimoto, Otawara (JP); Kazumasa Arakita, Nasushiobara (JP); Yoshihiro Ikeda, Sakura (JP); Shinsuke Tsukagoshi, Nasushiobara (JP); Yasuko Fujisawa, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 199 days.

(21) Appl. No.: 13/766,983

(22) Filed: Feb. 14, 2013

(65) Prior Publication Data

US 2013/0208855 A1    Aug. 15, 2013

(30) Foreign Application Priority Data

Feb. 14, 2012  (JP) ................. 2012-029298
Feb. 14, 2012  (JP) ................. 2012-029313
Feb. 24, 2012  (JP) ................. 2012-038313

(51) Int. Cl.
  *A61B 6/00*    (2006.01)

(52) U.S. Cl.
  CPC ............... *A61B 6/463* (2013.01); *A61B 6/5229* (2013.01); *A61B 6/5247* (2013.01); *A61B 6/461* (2013.01); *A61B 6/5288* (2013.01); *A61B 6/542* (2013.01)

(58) Field of Classification Search
  CPC .. A61B 6/5229; A61B 6/5247; A61B 6/5288; A61B 6/463
  USPC ................................. 378/63, 98.12
  See application file for complete search history.

(56) References Cited

U.S. PATENT DOCUMENTS

2009/0080598 A1*  3/2009  Tashman et al. ............ 378/11
2010/0061610 A1*  3/2010  Van De Haar ............ 382/131

(Continued)

FOREIGN PATENT DOCUMENTS

| CN | 102245106 A | 11/2011 |
|---|---|---|
| JP | 2010-259653 | 11/2010 |
| JP | 2011-4966 | 1/2011 |

OTHER PUBLICATIONS

Combined Chinese Office Action and Search Report issued Aug. 7, 2014 in Patent Application No. 201310047413.0 (with English translation of categories of cited documents).

(Continued)

*Primary Examiner* — Glen Kao
(74) *Attorney, Agent, or Firm* — Oblon, McClelland, Maier & Neustadt, L.L.P.

(57) ABSTRACT

Provided is a medical image diagnostic apparatus, including: an internal image acquiring unit for acquiring a plurality of internal images different in time phase by irradiating a body part of a subject with X-rays; an outer appearance image acquiring unit for acquiring an outer appearance image by photographing the body part of the subject; an analysis unit for analyzing the outer appearance image to acquire first shape information indicating a shape of the body part of the subject and analyzing each of the plurality of internal images to acquire second shape information indicating a shape of the body part of the subject; and a display control unit for displaying the outer appearance image and the each of the plurality of internal images by superimposing one on another so that the body part of the subject included in the outer appearance image and the body part of the subject included in the each of the plurality of internal images are located in the same position based on the first shape information and the second shape information.

25 Claims, 21 Drawing Sheets

(56) References Cited

U.S. PATENT DOCUMENTS

2010/0128841 A1* 5/2010 Imas et al. .................... 378/16
2010/0284628 A1 11/2010 Uebayashi et al.
2012/0008741 A1* 1/2012 Hendriks et al. ............... 378/63

OTHER PUBLICATIONS

U.S. Appl. No. 13/766,184, filed Feb. 13, 2013, Kimoto, et al.

* cited by examiner

MEDICAL IMAGE DIAGNOSTIC APPARATUS

CROSS-REFERENCE TO RELATED APPLICATION

This application is based upon and claims the benefit of priority from Japanese Patent Applications No. 2012-029298 and No. 2012-029313, filed on Feb. 14, 2012 and No. 2012-038313, filed on Feb. 24, 2012; the entire contents of which are incorporated herein by reference.

FIELD

Embodiments relate to a medical image diagnostic apparatus.

BACKGROUND

A medical image diagnostic apparatus is an apparatus for acquiring an image expressing an internal portion of a subject. An X-ray computed tomography (CT) apparatus and an X-ray machine are known as the medical image diagnostic apparatus.

The X-ray CT apparatus is an apparatus for imaging the internal portion of the subject by scanning the subject with X-rays, collecting data, and processing the collected data by using a computer. Specifically, the X-ray CT apparatus exposes the subject to X-rays from different directions a plurality of times, detects the X-rays that have passed through the subject by using an X-ray detector, and collects a plurality of detection data pieces. The collected detection data pieces are A/D-converted by a data collecting unit and then transmitted to a data processing system. The data processing system forms projection data by subjecting the detection data to pre-processing or the like. Subsequently, the data processing system executes reconstruction processing based on the projection data to form tomographic image data.

As further reconstruction processing, the data processing system forms volume data based on a plurality of tomographic image data pieces. The volume data is a data set indicating a three-dimensional distribution of a CT value corresponding to a three-dimensional area of the subject. In a case of acquiring the volume data, a volume scan using a multi-row type X-ray detector is employed. Further, by repeatedly performing the volume scan, it is possible to acquire a plurality of volume data pieces different in time phase (4D scan).

The X-ray CT apparatus can perform multi planar reconstruction (MPR) display by rendering the volume data in an arbitrary direction. An MPR-displayed cross-sectional image (MPR image) is classified into an orthogonal three-axis image and an oblique image. The orthogonal three-axis image represents an axial image indicating an orthogonal cross-section to a body axis, a sagittal image indicating a cross-section obtained by vertically cutting the subject along the body axis, and a coronal image indicating a cross-section obtained by horizontally cutting the subject along the body axis. The oblique image is an image indicating a cross-section other than the orthogonal three-axis image. Further, the X-ray CT apparatus sets an arbitrary line of sight and renders the volume data, to thereby form a pseudo three-dimensional image obtained when the three-dimensional area of the subject is viewed from the arbitrary line of sight.

Further, the X-ray machine is an apparatus for imaging the internal portion of the subject by irradiating the subject with X-rays and detecting the X-rays that have passed therethrough by using a two-dimensional X-ray detector. A photography method using the X-ray machine is classified into normal photographing for obtaining a still image by single X-ray application and fluoroscopy for obtaining the moving image by applying X-rays continuously or intermittently.

DETAILED DESCRIPTION

Embodiments provide a medical image diagnostic apparatus capable of obtaining a relationship between an action state of a body and an occurrence timing of a biological reaction.

The medical image diagnostic apparatus according to the embodiments includes: an internal image acquiring unit for acquiring a plurality of internal images different in time phase by irradiating a body part of a subject with X-rays; an outer appearance image acquiring unit for acquiring an outer appearance image by photographing the body part of the subject; an analysis unit for analyzing the outer appearance image to acquire first shape information indicating a shape of the body part of the subject and analyzing each of the plurality of internal images to acquire second shape information indicating a shape of the body part of the subject; and a display control unit for displaying the outer appearance image and the each of the plurality of internal images by superimposing one on another so that the body part of the subject included in the outer appearance image and the body part of the subject included in the each of the plurality of internal images are located in the same position based on the first shape information and the second shape information.

The medical image diagnostic apparatus according to the embodiments is described with reference to the accompanying drawings. The following description is directed to an example of an X-ray CT apparatus and an X-ray imaging apparatus.

First Embodiment

A configuration example of an X-ray CT apparatus 1 according to a first embodiment is described with reference to FIGS. 1 and 2. Note that, the terms "image" and "image data" may be regarded as having the same meaning.

Figure 1:
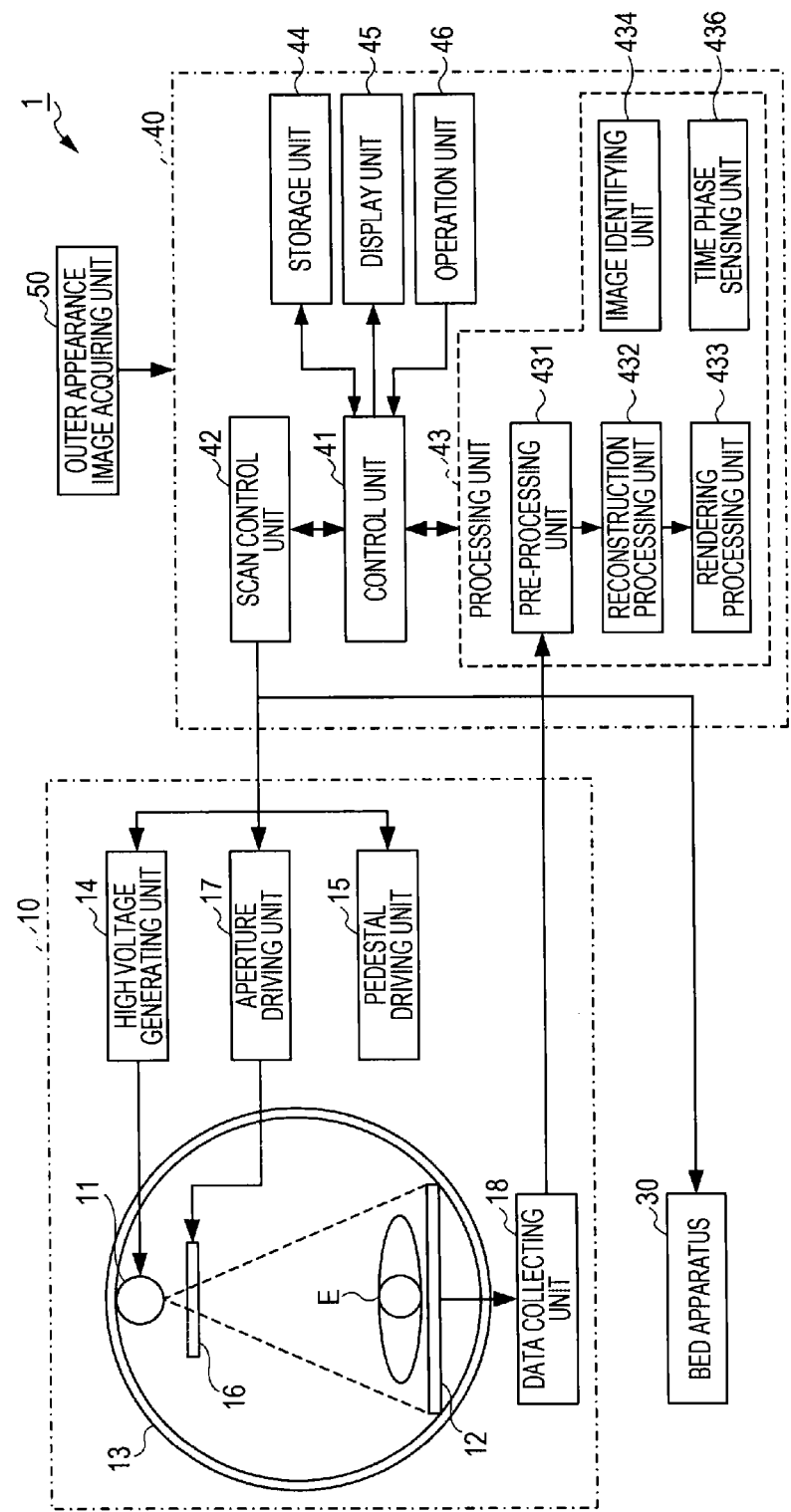
FIG. 1 is a block diagram illustrating a configuration of a medical image diagnostic apparatus (X-ray CT apparatus) according to a first embodiment.

FIG. 1 illustrates an overall configuration of the X-ray CT apparatus 1. In FIG. 2, components relating to acquisition of a CT image are collectively illustrated as an internal image acquiring unit 100. The internal image acquiring unit 100 includes a pedestal apparatus 10, a bed apparatus 30, a scan control unit 42, a pre-processing unit 431, and a reconstruction processing unit 432 that are illustrated in FIG. 1. Further, in a case where the reconstruction processing unit 432 forms volume data, the internal image acquiring unit 100 also includes a rendering processing unit 433.

This embodiment is described by taking the X-ray CT apparatus as an example, but can be applied to an MRI apparatus instead of the X-ray CT apparatus. The MRI apparatus uses a nuclear magnetic resonance (NMR) phenomenon to magnetically excite nuclear spins within a desired body part to be examined of the subject placed in a static magnetic field with a radio-frequency signal having a Larmor frequency, measures a density distribution, a relaxation time distribution, or the like based on a free induction decay (FID) signal and an echo signal that occur along with the excitement, and displays an image of an arbitrary cross-section of the subject based on data on measurement thereof.

As illustrated in FIG. 1, the X-ray CT apparatus 1 includes the pedestal apparatus 10, the bed apparatus 30, a console device 40, and an outer appearance image acquiring unit 50.

(Pedestal Apparatus)

The pedestal apparatus 10 is an apparatus for exposing a subject E to X-rays and collecting detection data on the X-rays that have passed through the subject E. The pedestal apparatus 10 includes an X-ray generating unit 11, an X-ray detecting unit 12, a rotary member 13, a high voltage generating unit 14, a pedestal driving unit 15, an X-ray aperture unit 16, an aperture driving unit 17, and a data collecting unit 18.

The X-ray generating unit 11 includes an X-ray tube (for example, a vacuum tube (not shown) for generating a cone-shaped beam or a pyramid-shaped beam) for generating X-rays. The subject E is exposed to the generated X-ray.

The X-ray detecting unit 12 includes a plurality of X-ray detecting elements (not shown). The X-ray detecting unit 12 uses the X-ray detecting element to detect X-ray intensity distribution data (hereinafter referred to also as "detection data") indicating an intensity distribution of the X-rays that have passed through the subject E, and outputs the detection data as a current signal.

As the X-ray detecting unit 12, for example, a two-dimensional X-ray detector (planar detector) in which a plurality of detection elements are arranged along each of two directions (slice direction and channel direction) orthogonal to each other is used. As the plurality of X-ray detecting elements, for example, 320 rows are provided along the slice direction. By thus using a multi-row X-ray detector, a three-dimensional area having a width in the slice direction can be photographed with a scan of one rotation (volume scan). Note that, the slice direction corresponds to a body axis direction of the subject E, and the channel direction corresponds to a rotational direction of the X-ray generating unit 11.

The rotary member 13 is a member for supporting the X-ray generating unit 11 and the X-ray detecting unit 12 in positions opposed to each other across the subject E. The rotary member 13 includes an opening portion that penetrates in the slice direction. A top board on which the subject E is placed is inserted into the opening portion. The rotary member 13 is caused to rotate along a circular trajectory about the subject E by the pedestal driving unit 15.

The high voltage generating unit 14 applies a high voltage to the X-ray generating unit 11. The high voltage is defined by parameters such as the tube voltage, the tube current, and an application time (photographing time). The X-ray generating unit 11 generates X-rays based on the high voltage. The X-ray aperture unit 16 forms a slit (opening), and changes a size and a shape of the slit, to thereby adjust a fan angle (angle of divergence in the channel direction) of the X-rays output from the X-ray generating unit 11 and a cone angle (angle of divergence in the slice direction) of the X-rays. The aperture driving unit 17 drives the X-ray aperture unit 16 to change the size and the shape of the slit.

The data collecting unit 18 (data acquisition system; DAS) collects the detection data from the X-ray detecting unit 12 (each of the X-ray detecting elements). In addition, the data collecting unit 18 converts the collected detection data (current signal) into a voltage signal, integrates and amplifies the voltage signal periodically, and converts the resultant into a digital signal. Then, the data collecting unit 18 transmits the detection data that has been converted into the digital signal to the console device 40.

(Bed Apparatus)

The subject E is placed on the top board (not shown) of the bed apparatus 30. The bed apparatus 30 causes the subject E placed on the top board to move in the body axis direction. Further, the bed apparatus 30 causes the top board to move in a vertical direction.

(Console Device)

The console device 40 is used to input an operation to the X-ray CT apparatus 1. Further, the console device 40 reconstructs CT image data (tomographic image data and volume data) indicating an internal form of the subject E from the detection data input from the pedestal apparatus 10. The console device 40 includes a control unit 41, the scan control unit 42, a processing unit 43, a storage unit 44, a display unit 45, and an operation unit 46.

The control unit 41, the scan control unit 42, and the processing unit 43 include, for example, a processing device and a storage device. As the processing device, for example, a central processing unit (CPU), a graphic processing unit (GPU), or an application specific integrated circuit (ASIC) is used. The storage device includes, for example, a read only memory (ROM), a random access memory (RAM), and a hard disc drive (HDD).

Computer programs for executing functions of respective components of the X-ray CT apparatus 1 are stored on the storage device. The processing device realizes the above-mentioned functions by executing those computer programs. The control unit 41 controls the respective components of the X-ray CT apparatus 1.

The scan control unit 42 integrally controls operations relating to the scan using X-rays. The integral control includes control of the high voltage generating unit 14, control of the pedestal driving unit 15, control of the aperture driving unit 17, and control of the bed apparatus 30.

In the control of the high voltage generating unit 14, the high voltage generating unit 14 is controlled so as to apply a predetermined high voltage to the X-ray generating unit 11 at a predetermined timing. In the control of the pedestal driving unit 15, the pedestal driving unit 15 is controlled so as to rotationally drive the rotary member 13 with a predetermined speed at a predetermined timing. In the control of the aperture driving unit 17, the aperture driving unit 17 is controlled so that the X-ray aperture unit 16 forms the slit having a predetermined size and a predetermined shape. In the control of the bed apparatus 30, the bed apparatus 30 is controlled so as to move the top board in a predetermined position at a predetermined timing.

Note that, in the volume scan, a scan is executed with the top board fixed in position. Further, in a helical scan, a scan is executed with the top board being moved.

The processing unit 43 executes various kinds of processing on the data input from the pedestal apparatus 10 (the data collecting unit 18) and the data input from the outer appearance image acquiring unit 50. The processing unit 42 includes the pre-processing unit 431, the reconstruction processing unit 432, the rendering processing unit 433, an image identifying unit 434, and a time phase sensing unit 436.

The pre-processing unit 431 generates projection data by executing pre-processing on the detection data input from the pedestal apparatus 10. The pre-processing includes logarithmic conversion processing, offset cancellation, sensitivity correction, and beam hardening correction.

The reconstruction processing unit 432 generates the CT image data (tomographic image data and volume data) based on the projection data generated by the pre-processing unit 431. As reconstruction processing for the tomographic image data, an arbitrary method including, for example, a two-dimensional Fourier transform method or a convolution back-projection method can be employed.

The volume data is generated by performing interpolation processing on a plurality of tomographic image data pieces that have been reconstructed. As the reconstruction processing for the volume data, an arbitrary method including, for example, a cone beam reconstruction method, a multi-slice reconstruction method, or an enlargement reconstruction method can be employed. In the volume scan using the above-mentioned multi-row X-ray detector, it is possible to reconstruct the volume data within a wide range.

The rendering processing unit 433 can execute, for example, MPR processing and volume rendering. The MPR processing is image processing for setting an arbitrary cross-section for the volume data generated by the reconstruction processing unit 432 and subjecting the cross-section to rendering processing, to thereby generate an MPR image data indicating the cross-section. The volume rendering is image processing for sampling the volume data along an arbitrary line of sight (ray) and accumulating values (CT values) thereof, to thereby generate pseudo three-dimensional image data indicating the three-dimensional area of the subject E.

(Image Identifying Unit)

First, a description is made of matters on which the processing executed by the image identifying unit 434 is predicated. The image (CT image) formed by the reconstruction processing unit 432 is referred to as "internal image", and the image acquired by the outer appearance image acquiring unit 50 is referred to as "outer appearance image". The internal image is an image that represents an interior of the subject E. Further, the outer appearance image is an image that represents an outer appearance of the subject E.

The internal image acquiring unit 100 continuously or intermittently irradiates a predetermined body part of the subject E with X-rays to acquire the plurality of internal images. The predetermined body part is, for example, a joint part. Examples of the plurality of internal images include a plurality of volume data pieces along time series obtained by a 4D scan, a pseudo three-dimensional image or a plurality of tomographic images along time series obtained by rendering those volume data pieces, and a plurality of tomographic images along time series obtained by repeatedly scanning a predetermined cross-section.

The operation unit 46 is used to input occurrence information indicating an occurrence of the biological reaction of the subject E. The biological reaction includes one that occurs along with a pain. Examples of the biological reaction that occurs along with a pain include recognition of the pain, utterance, a change in facial expression, a change in respiration, a change in perspiration, a change in electrocardiogram, a change in blood pressure, a change in electromyogram, a change in electroencephalogram, and a change in pupil diameter.

An operator of the operation unit 46 operates the operation unit 46 in response to the occurrence of such a biological reaction. The operation unit 46 that has received the operation inputs a signal serving as the occurrence information to the control unit 41. Note that, the operator is the subject E (patient) or another person (such as doctor, nurse, or radiological technologist).

The outer appearance image acquiring unit 50 acquires the outer appearance image by photographing the predetermined body part of the subject E at a photographing timing corresponding to the input of the occurrence information. The photographing may be any one of still image photographing and moving image photographing. The outer appearance image acquiring unit 50 is described later in detail. An example of photographing the outer appearance image at the same timing as the input of the occurrence information and acquiring the internal image obtained at the same timing is described, but it is not always necessary to synchronize those timings. The outer appearance image may be photographed irrespective of the input of the occurrence information, or the internal image may be identified irrespective of the photographing timing for the outer appearance image. Further, the timings for the input of the occurrence information, the photographing of the outer appearance image, and the internal image may be included within a time width to some extent.

With the above-mentioned preparations made, the image identifying unit 434 is described. The image identifying unit 434 identifies the internal image acquired at substantially the same time as the input of the occurrence information among the plurality of internal images acquired by the internal image acquiring unit 100. The control unit 41 stores the identified internal image and the outer appearance image acquired at the photographing timing corresponding to the input of the occurrence information on the biological reaction in the storage unit 44 in association with each other.

Further, in a case where the outer appearance image acquiring unit 50 performs the moving image photographing or performs the still image photographing a plurality of times, the image identifying unit 434 identifies, along with the above-mentioned internal image, the outer appearance image acquired at substantially the same time as the input of the occurrence information on the biological reaction among the outer appearance images acquired sequentially by the moving image photographing. Processing for identifying the outer appearance image can be executed in the same manner as processing for identifying the internal image. The control unit 41 stores the identified internal image and the identified outer appearance image in the storage unit 44 in association with each other.

With the above-mentioned preparations made, another example of the image identifying unit 434 is described. The image identifying unit 434 includes a function of identifying the internal image acquired at substantially the same time as the input of the occurrence information (first identification unit) and a function of identifying the outer appearance image acquired at substantially the same time as the input of the occurrence information (second identification unit). Those functions are now described.

The image identifying unit 434 identifies the internal image acquired at substantially the same time as the input of the occurrence information among the plurality of internal images acquired by the internal image acquiring unit 100. Note that, as described later, the processing for identifying the internal image may include the processing for identifying the outer appearance image. The control unit 41 stores the identified internal image, the outer appearance image acquired at the photographing timing corresponding to the input of the occurrence information on the biological reaction, and timing information indicating the occurrence timing of the biological reaction, in the storage unit 44 in association with one another.

Examples of the timing information include image information or character string information indicating the occurrence timing of the biological reaction and a flag indicating the occurrence timing. Examples of the character string information include a file name of each image data on the internal image and the outer appearance image and a folder name of a folder that stores each image data. Further, examples of the image information include image data stored along with each image data on the internal image and the outer appearance image and information superimposed on each image data.

Further, as in the case where the outer appearance image acquiring unit 50 performs the moving image photographing or performs the still image photographing a plurality of times, in a case where the predetermined body part of the subject E is repeatedly photographed, the image identifying unit 434 identifies the outer appearance image acquired at substantially the same time as the input of the occurrence information on the biological reaction among the sequentially-acquired outer appearance images. The processing for identifying the outer appearance image can be executed in the same manner as the processing for identifying the internal image. The control unit 41 stores the identified outer appearance image and the above-mentioned timing information in the storage unit 44 in association with each other. In addition, the control unit 41 stores at least one of the plurality of internal images acquired by the internal image acquiring unit 100 in the storage unit 44. The internal image to be stored may be the internal image identified as described above, at least one internal image selected by another method, or all the plurality of internal images.

The wording "substantially the same time" not only represents completely the same time but also allows an arbitrarily-set error. The error is determined based on, for example, an acquisition interval for at least one of the internal image and the outer appearance image. An example of the processing executed by the image identifying unit 434 is described. In the following example, a predetermined joint part of the subject E is to be examined. The internal image and the outer appearance image are obtained by photographing a range including the range including the joint part.

Figure 2:
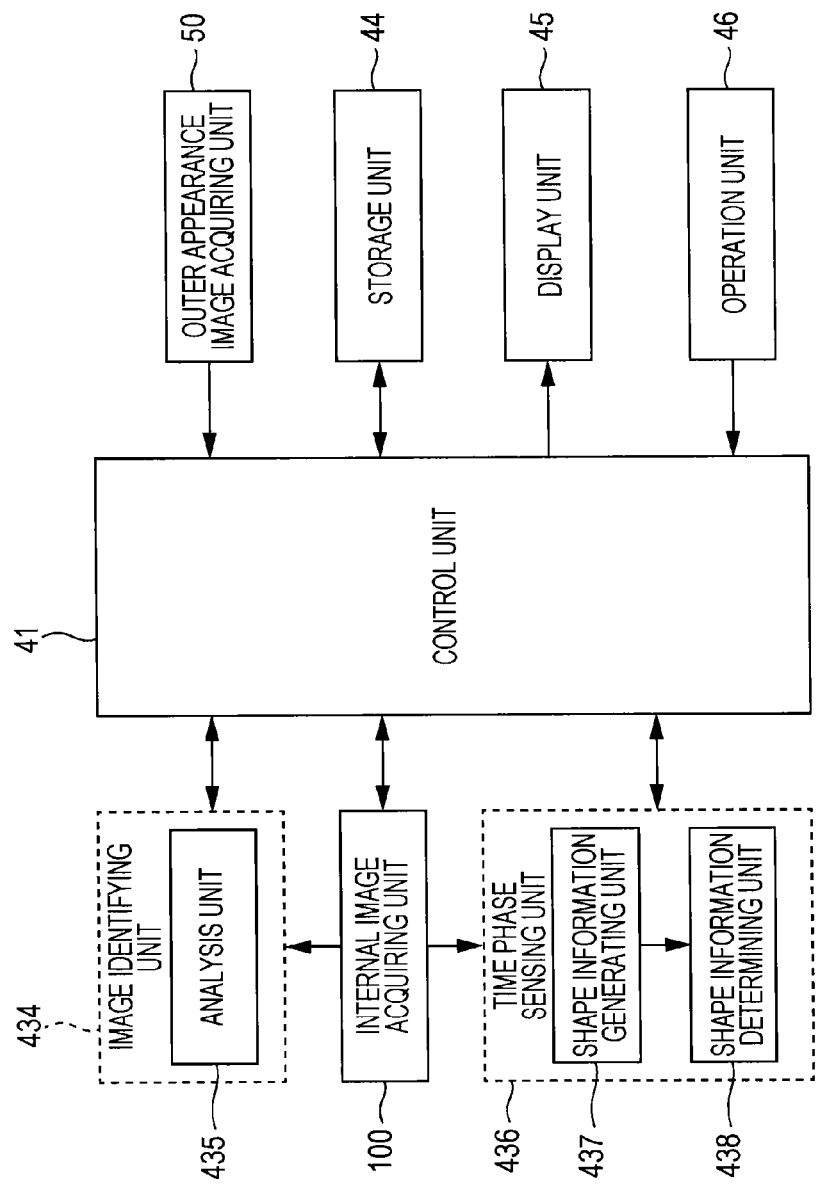
FIG. 2 is a block diagram illustrating the configuration of the medical image diagnostic apparatus (X-ray CT apparatus) according to the first embodiment.

In a case where a first processing example is employed, the image identifying unit 434 includes an analysis unit 435 as illustrated in FIG. 2. The analysis unit 435 analyzes the outer appearance image acquired by the outer appearance image acquiring unit 50, to thereby acquire the first shape information indicating a shape of the joint part. In addition, the analysis unit 435 analyzes each of the plurality of internal images acquired by the internal image acquiring unit 100, to thereby acquire the second shape information indicating the shape of the joint part drawn in the internal image.

Here, in the internal image and the outer appearance image, the joint part is drawn from (substantially) the same direction. As a method of realizing this, a drawing direction of the outer appearance image can be matched with a drawing direction of the internal image, and vice versa. The former is employed in the case of using the X-ray machine, and can be realized by, for example, providing a photography apparatus for the outer appearance image in the vicinity of the X-ray tube or the X-ray detector.

The latter is employed in the case of, for example, forming the volume data, and can be realized by rendering the volume data on the tomographic image of the cross-section corresponding to the drawing direction of the outer appearance image. As an example of a method of identifying the cross-section, a data range correspond to the joint part is identified in the volume data, and a two-dimensional data range that (substantially) matches the shape of a two-dimensional area corresponding to the joint part in the outer appearance image within a three-dimensional data range thereof is identified by using the image processing such as the pattern matching, which enables an orientation of the two-dimensional data range in the coordinate system defined in the volume data to be set as an orientation of an object cross-section.

Figure 3:
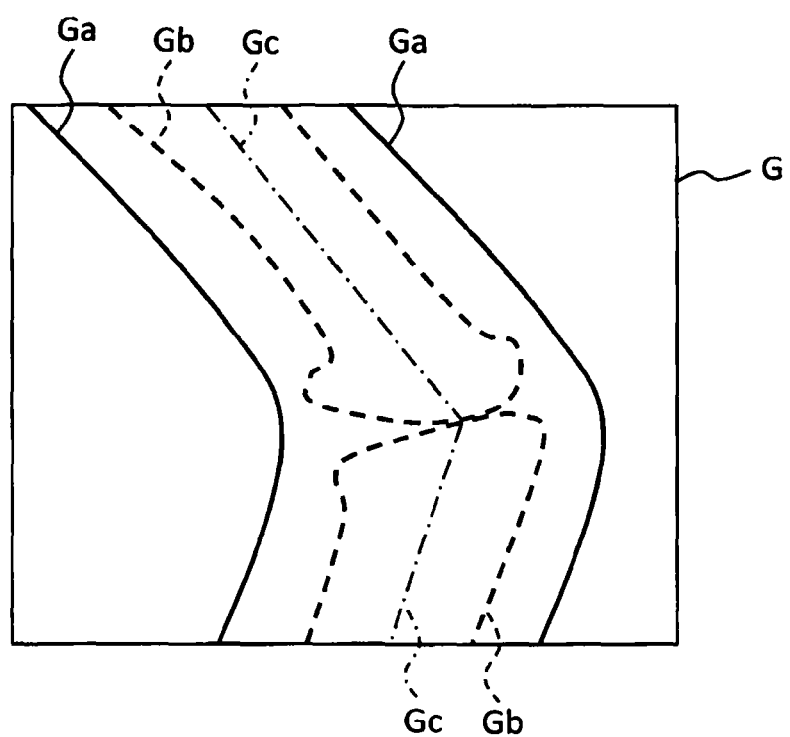
FIG. 3 illustrates processing executed by the medical image diagnostic apparatus (X-ray CT apparatus) according to the first embodiment.

Each of shape information represents, for example, a shape of a contour of a body surface within the range including the joint part. In this case, the analysis unit 435 identifies the image area having, for example, a predetermined color (skin color) or predetermined shapes (shapes of the joint part and the surrounding body part) based on a pixel value (such as brightness value, RGB value, or CT value) of each image. In addition, the analysis unit 435 identifies the image area (contour area) corresponding to the contour of the image area. As an example of this case, FIG. 3 illustrates a contour area Ga within a CT image G. The contour area itself or the shape (including an approximate shape) corresponds to the first shape information and the second shape information.

The shape information is not limited to a contour shape, and any shape that indicates the shape of the joint part may suffice. For example, the contour shape of a bone and a core line shape thereof can be used as the shape information. As an example of those cases, FIG. 3 illustrates a contour area Gb of a bone and a core line area Gc thereof within the CT image G. Note that, in the case of using the core line shape, an angle formed by core lines of at least two bones located in the joint part may be obtained, and angle information thereon may be set as the shape information. Also in the case of using the contour shape, each of directions of two body parts (for example, upper arm and forearm in the case of the elbow joint) contacting with each other in the joint part may be identified based on the contour shape and an angle formed by those two directions may be obtained, and the angle information thereon may be set as the shape information.

The analysis unit 435 performs the above-mentioned processing on each of the plurality of internal images acquired by the internal image acquiring unit 100. Accordingly, a plurality of second shape information pieces are obtained. The image identifying unit 434 identifies the internal image corresponding to a second shape information piece that substantially matches the first shape information based on the outer appearance image among the plurality of second shape information pieces that have been obtained. This processing can be performed by, for example, subjecting the first shape information and the second shape information to the image processing such as the pattern matching. The internal image identified in such a manner is used as the internal image acquired at substantially the same time as the input of the occurrence information on the biological reaction.

A second processing example is described. Also in a case where this processing example is employed, the image identifying unit 434 includes the analysis unit 435 as illustrated in FIG. 2. The analysis unit 435 analyzes the outer appearance image acquired by the outer appearance image acquiring unit 50, to thereby acquire first feature position information indicating a position of a predetermined feature area within the outer appearance image. In addition, the analysis unit 435 analyzes each of the plurality of internal images acquired by the internal image acquiring unit 100, to thereby acquire second feature position information indicating the position of the feature area within the internal image.

The feature area is an image area corresponding to a predetermined body part of a human body or an image area corresponding to an artifact photographed along with the subject E. Examples of the former include a predetermined bone or a predetermined body part thereof and a predetermined organ or a predetermined body part thereof. Further, examples of the latter include a marker attached to the subject E, an insertion (such as catheter) inserted into the subject E, and the artifact (such as bolt for connecting bones) provided to the interior of the subject E.

Processing for identifying the feature area can be, for example, performed by the pattern matching based on the shape of the feature area or performed based on the pixel value (such as brightness value, RGB value, or CT value) unique to the feature area. Further, the number of feature areas to be identified is an arbitrary number of at least one. In a case of identifying at least two feature areas, information indicating a positional relationship (such as distance and direction) between those feature areas can be set as feature position information.

Further, each feature area may be any one of one point (one pixel) and an image area formed of a plurality of pixels. In a case of the latter, the information indicating the size and the shape of the image area can be set as the feature position information.

The analysis unit 435 performs the above-mentioned processing on each of the plurality of internal images acquired by the internal image acquiring unit 100. Accordingly, a plurality of second feature position information pieces are obtained. The image identifying unit 434 identifies the internal image acquired at substantially the same time as the input of the occurrence information on the biological reaction based on the obtained plurality of second feature position information pieces and the first feature position information based on the outer appearance image.

This processing can be performed by, for example, comparing the first feature position information with the second feature position information to select the second feature position information indicating the feature area having (substantially) the same positional relationship as the positional relationship between at least two feature areas indicated by the first feature position information, (substantially) the same size or shape as those of the feature area indicated by the first feature position information, or the like. The internal image corresponding to the selected second feature position information is used as the internal image acquired at substantially the same time as the input of the occurrence information on the biological reaction.

A third processing example is described. In a case where this processing example is employed, there is no need to provide the analysis unit 435 to the image identifying unit 434 as illustrated in FIG. 1. In the case of performing this processing example, the image identifying unit 434 receives first input timing information indicating a timing at which the occurrence information on the biological reaction is input by the operation unit 46 and second input timing information indicating a timing at which the internal image is acquired by the internal image acquiring unit 100. Then, the image identifying unit 434 identifies the internal image corresponding to the second input timing information received at substantially the same time as the first input timing information.

The first input timing information is sent from the control unit 41 to the image identifying unit 434 in response to the input of the signal from the operation unit 46 to the control unit 41. The second input timing information is input to the image identifying unit 434 every time the internal image of each time phase is formed or every time the scan of each time phase is performed.

In a case where time required for the pre-processing and the reconstruction processing is sufficiently short, the second input timing information is input to the image identifying unit 434 from any one of the reconstruction processing unit 432, the rendering processing unit 433, the control unit 41, and the pedestal apparatus 10 at any one of timings for image formation and scanning. Otherwise, the second input timing information is input to the image identifying unit 434 from the control unit 41 or the pedestal apparatus 10 at a timing at which a scan is performed.

The second input timing information is successively input to the image identifying unit 434. The image identifying unit 434 that has received the input of the first input timing information corresponding to operation of the operation unit 46 identifies the second input timing information input at, for example, the closest timing to the input timing for the first input timing information. Then, the image identifying unit 434 sets the internal image corresponding to the identified second input timing information as the internal image acquired at substantially the same time as the input of the occurrence information on the biological reaction.

(Time Phase Sensing Unit)

The internal image acquiring unit 100 acquires a new internal image based on the outer appearance image and the timing information stored in the storage unit 44 under control of the control unit 41. The time phase sensing unit 436 operates in this processing. Two examples of this processing are now described.

In a first processing example, based on the outer appearance image and the timing information stored in the storage unit 44, the internal image acquiring unit 100 acquires the new internal image in a specific time phase corresponding to the timing information. The "specific time phase" is described. The timing information indicates the occurrence timing of the biological reaction. The specific time phase corresponds to a state of the predetermined body part (for example, bent state of the joint) of the subject E at the occurrence timing of the biological reaction. The specific time phase is not necessarily a time phase that completely matches the state of the predetermined body part, and allows an arbitrarily-set error. Further, the specific time phase does not need to be a single time phase and may be at least two time phases.

In this processing example, the internal image acquiring unit 100 executes photographing using X-rays having a first intensity and photographing using X-rays having a second intensity while switching therebetween. The second intensity is lower than the first intensity. The switching is executed by controlling the above-mentioned parameters of the high voltage applied to the X-ray generating unit 11 from the high voltage generating unit 14. The internal image acquiring unit 100 applies the X-rays having the first intensity in the specific time phase, and applies the X-rays having the second intensity in the time phase other than the specific time phase. Accordingly, a plurality of new internal images corresponding to a plurality of time phases including the specific time phase are acquired. In other words, the internal image acquiring unit 100 performs the photographing with X-rays having a relatively high intensity in the specific time phase, and performs the photographing with X-rays having a relatively low intensity in the time phase other than the specific time phase.

The time phase sensing unit 436 determines a timing to switch an X-ray intensity in such processing. In order to execute this processing, the time phase sensing unit 436 includes a shape information generating unit 437 and a shape information determining unit 438. The shape information generating unit 437 functions as an example of a "generation unit", and the shape information determining unit 438 functions as an example of a "determination unit".

With regard to the processing executed by the time phase sensing unit 436, a first specific example and a second specific example are described. In both the first and second specific examples, the time phase sensing unit 436 compares a newly-acquired image with the outer appearance image acquired in the past. In the first specific example, the newly-acquired internal image is used, and in the second specific example, the newly-acquired outer appearance image is used.

The first specific example is described. In the first specific example, the time phase sensing unit 436 senses arrival of the specific time phase by comparing the new internal image acquired by applying the X-rays having the second intensity (relatively low intensity) with the outer appearance image stored in the storage unit 44.

This processing is described more specifically. First, the shape information generating unit 437 analyzes each of the new internal image acquired by applying the X-rays having the second intensity and the outer appearance image stored in the storage unit 44, and generates predetermined body part shape information indicating the shape of the predetermined body part of the subject E. This processing includes, for example, the same processing as the processing executed by the image identifying unit 434. Note that, a part relating to the same processing may be executed by the image identifying unit 434. Examples of the same processing include processing for obtaining the contour, the core line, the angle, and the like of the predetermined body part within the image (the above-mentioned first processing example) and processing for obtaining the position of the feature area within the image (the above-mentioned second processing example). In those cases, the predetermined body part shape information is information indicating the shape of the contour of the predetermined body part, the shape of the core line thereof, the angle information thereon, or the positional relationship of the feature area.

The shape information determining unit 438 determines whether or not the predetermined body part shape information generated from the new internal image and the predetermined body part shape information generated from the outer appearance image stored in the storage unit 44 substantially match each other. The determination processing is the same processing as, for example, the above-mentioned pattern matching executed by the image identifying unit 434. In that case, this processing may be executed by the image identifying unit 434.

When the shape information determining unit 438 determines that the above-mentioned pieces of predetermined body part shape information substantially match each other, the time phase sensing unit 436 determines that the specific time phase has arrived. In response to the fact that the time phase sensing unit 436 has sensed the arrival of the specific time phase, the control unit 41 controls the internal image acquiring unit 100 to switch from the second intensity to the first intensity.

The second specific example is described. In the second specific example, the time phase sensing unit 436 senses the arrival of the specific time phase by comparing the new outer appearance image acquired by the outer appearance image acquiring unit 50 with the outer appearance image stored in the storage unit 44. Detailed description of this processing is omitted because the internal image used in the first specific example is merely replaced by the outer appearance image. This is the end of the description of the first processing example.

Next, a second processing example is described. In this processing example, based on the outer appearance image and the timing information stored in the storage unit 44, the internal image acquiring unit 100 acquires the new internal image during a predetermined period including the time phase corresponding to the timing information.

The first and second processing examples are different in the time phase in which the new internal image is to be acquired. In other words, in the first processing example, new photographing is performed in the specific time phase corresponding to the stored timing information, while in the second processing example, the new photographing is performed not only in the specific time phase but also during the predetermined period including the specific time phase.

The predetermined period is described. The predetermined period may begin from or end at the specific time phase, or another option may be applied. In the case of beginning from the specific time phase, the predetermined period can be set by, for example, measuring a period having a length determined in advance since the arrival of the specific time phase.

In the case of ending at the specific time phase, for example, information indicating a predetermined time phase that arrives before the specific time phase is included in the timing information in advance. Then, a period since the arrival of the predetermined time phase until the arrival of the specific time phase can be set as the predetermined period. In the case of neither beginning from nor ending at the specific time phase stage, the predetermined period can be set by, for example, combining the above-mentioned two cases to determine a period before the specific time phase and a period thereafter.

In a case where there are a plurality of specific time phases, a period between those specific time phases can be set as the predetermined period. Further, the predetermined period may be formed of at least two periods. Each of those periods can be set, for example, in the above-mentioned manner.

Also in this processing example, in the same manner as the first processing example, the internal image acquiring unit 100 executes the photographing using the X-rays having the first intensity in the time phase included in the predetermined period, and executes the photographing using the X-rays having the second intensity in a time phase during a period other than the predetermined period, to thereby acquire a plurality of new internal images.

With regard to the switching of the X-ray intensity, the time phase sensing unit 436 performs the same processing as the first processing example. In other words, in the case of using the new internal image (corresponding to the above-mentioned first specific example), the time phase sensing unit 436 compares the new internal image acquired by applying the X-rays having the second intensity with the outer appearance image stored in the storage unit 44, to thereby sense the arrival of the time phase included in the predetermined period. Further, in the case of using the new outer appearance image (corresponding to the above-mentioned second specific example), the time phase sensing unit 436 compares the new outer appearance image acquired by the outer appearance image acquiring unit 50 with the outer appearance image stored in the storage unit 44, to thereby sense the arrival of the time phase included in the predetermined period.

In those processings, the shape information generating unit 437 and the shape information determining unit 438 perform the same processing as the first processing example to determine whether or not the pieces of predetermined body part shape information based on the two images substantially match each other, and when it is determined that the pieces of predetermined body part shape information substantially match each other, the time phase sensing unit 436 determines that an object time phase has arrived.

The object time phase is a time phase included in the above-mentioned predetermined period. The object time phase may be an arbitrary one of the time phases included in the predetermined period. For example, a case where a time phase other than the beginning stage and the end stage within the predetermined period is first sensed based on a speed of an action of the predetermined body part, a direction of the action, and time required for the photographing or the processing is assumed. In this processing example, even in such a case, it can be determined whether or not the time phase is included in the predetermined period.

In response to the fact that the time phase sensing unit 436 has sensed the arrival of the specific time phase, the control unit 41 controls the internal image acquiring unit 100 to switch from the second intensity to the first intensity.

(Storage Unit, Display Unit, and Operation Unit)

The storage unit 44 stores the detection data, the projection data, the image data obtained after the reconstruction processing, and the like. The display unit 45 is formed of a display device such as a liquid crystal display (LCD). The operation unit 46 is used to input various kinds of information and various instructions to the X-ray CT apparatus 1. The operation unit 46 is formed of, for example, a keyboard, a mouse, a trackball, a joystick, and the like. Further, the operation unit 46 may include a graphical user interface (GUI) displayed on the display unit 45.

As described above, the operation unit 46 is used to input the occurrence information indicating the occurrence of the biological reaction of the subject E. In other words, in response to the operation performed by the operator, the operation unit 46 inputs the signal serving as the occurrence information on the biological reaction. The operation unit 46 thus functions as an "input unit".

(Outer Appearance Image Acquiring Unit)

The outer appearance image acquiring unit 50 acquires the outer appearance image by photographing the predetermined body part (such as joint part) of the subject E at least at the photographing timing corresponding to the input of the occurrence information on the biological reaction. The photographing may be any one of the still image photographing and the moving image photographing. The outer appearance image acquiring unit 50 includes at least one of a digital camera and a digital video camera depending on a photographing manner thereof.

In the case of the still image photographing, the outer appearance image acquiring unit 50 can be configured to execute the photographing in response to the input of the occurrence information received from the operation unit 46. As an example thereof, the control unit 41 that has received the input of the occurrence information can be configured to control the outer appearance image acquiring unit 50 to perform the photographing.

Further, the control unit 41 that has received the input of the occurrence information can be configured to perform control for outputting alarm information to allow the operator who has recognized the alarm information to input a photographing trigger for the outer appearance image. Note that, the alarm information is, for example, display information output by the display unit 45 or audio information output by an audio output unit (not shown).

The outer appearance image obtained by the still image photographing corresponds to the outer appearance image acquired at the photographing timing corresponding to the input of the occurrence information on the biological reaction.

An arbitrary number of at least one outer appearance image is obtained by such still image photographing. In a case of acquiring at least two outer appearance images, at least one outer appearance image of those that includes a first-photographed one can be selected as the outer appearance image acquired at the photographing timing corresponding to the input of the occurrence information on the biological reaction. The selection processing includes, for example, processing for extracting the outer appearance image acquired during a time determined in advance and processing for extracting the outer appearance images whose number is determined in advance. Further, the outer appearance image that has been photographed since the start of the still image photographing until the photographing is requested to stop can also be used as the outer appearance image acquired at the photographing timing.

In a case of the moving image photographing, the outer appearance image acquiring unit 50 successively inputs a video signal obtained by repeatedly performing the photographing to the console device 40. Each frame obtained by the moving image photographing corresponds to the outer appearance image. Accordingly, a plurality of outer appearance images along time series are obtained.

(Operation)

An operation of the X-ray CT apparatus 1 according to this embodiment is described. First to fifth operation examples are described below. In the first operation example, the photographing is performed in the time phase corresponding to the occurrence timing of the biological reaction, and the outer appearance image acquiring unit 50 performs the still image photographing. In the second operation example, the photographing is performed during the predetermined period including the time phase corresponding to the occurrence timing of the biological reaction. In the third operation example, the photographing is performed by increasing the X-ray intensity in the time phase corresponding to the occurrence timing of the biological reaction. In the fourth operation example, the photographing is performed by increasing the X-ray intensity during the predetermined period including the time phase corresponding to the occurrence timing of the biological reaction. In the fifth operation example, the outer appearance image acquiring unit 50 performs the moving image photographing.

First Operation Example

In this operation example, the photographing is performed in the time phase corresponding to the occurrence timing of the biological reaction. In the following, processing for storing the image and the timing information is first described with reference to FIG. 4, and then the photographing based on the stored information is described with reference to FIG. 5. Note that, the former processing and the latter processing can be continuously performed (preliminary photographing and regular photographing) or can be performed on different dates/times.

Figure 4:
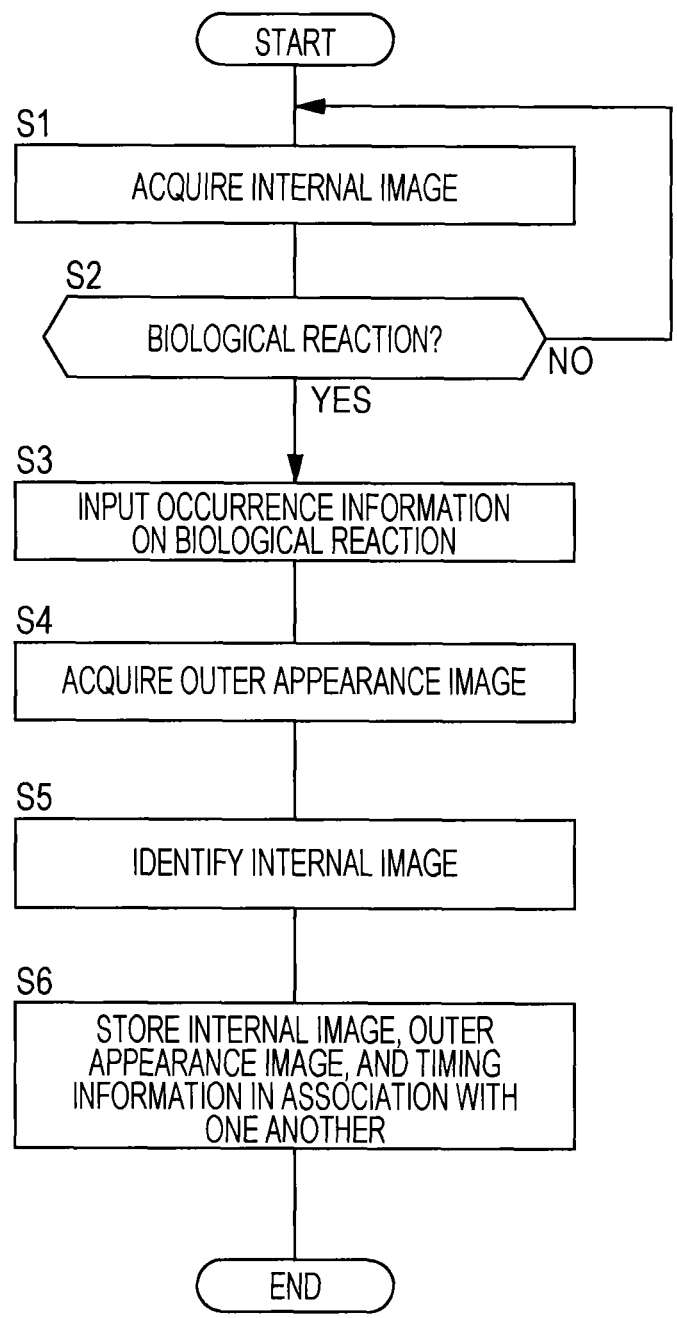
FIG. 4 is a flowchart illustrating a first operation example of the medical image diagnostic apparatus (X-ray CT apparatus) according to the first embodiment.

(Storage of Image and Timing Information: FIG. 4)

(S1: Acquire Internal Image)

The acquisition of the plurality of internal images different in time phase is started. The acquisition of the internal image is continued until at least the input of the occurrence information on the biological reaction (S3). Processing for acquiring the internal image is performed, for example, as follows.

First, the subject E is placed on the top board of the bed apparatus 30 and inserted into the opening portion of the pedestal apparatus 10. When a predetermined scan start operation is performed, the control unit 41 sends a control signal to the scan control unit 42. The scan control unit 42 that has received the control signal controls the high voltage generating unit 14, the pedestal driving unit 15, and the aperture driving unit 17 to scan the range including the predetermined body part of the subject E with X-rays. The X-ray detecting unit 12 detects the X-rays that have passed through the subject E. The data collecting unit 18 collects the detection data successively generated from the X-ray detecting unit 12 along with the progress of the scan. The data collecting unit 18 sends the collected detection data to the pre-processing unit 431. The pre-processing unit 431 performs the above-mentioned pre-processing on the detection data input from the data collecting unit 18 to generate the projection data. The reconstruction processing unit 432 subjects the projection data to the reconstruction processing based on a reconstruction condition set in advance, to thereby form the plurality of internal images different in time phase.

(S2 and S3: Input Occurrence Information on Biological Reaction)

When recognizing the occurrence of a predetermined biological reaction (S2: YES), the operator operates the operation unit 46. The operation unit 46 that has received the operation inputs the signal serving as the occurrence information on the biological reaction to the control unit 41 (S3).

(S4: Acquire Outer Appearance Image)

The control unit 41 that has received the input of the occurrence information on the biological reaction controls the outer appearance image acquiring unit 50 to photograph the predetermined body part of the subject E. Alternatively, the control unit 41 that has received the input of the occurrence information on the biological reaction causes predetermined alarm information to be output. The operator who has recognized the alarm information operates the operation unit 46 to instruct the acquisition of the outer appearance image. In response to the instruction, the outer appearance image acquiring unit 50 performs the photographing. Therefore, the outer appearance image is obtained.

(S5: Identify Internal Image)

The image identifying unit 434 executes any one of the above-mentioned processings, to thereby identify the internal image acquired at substantially the same time as the input of the occurrence information on the biological reaction (S3) among the plurality of internal images acquired in Step S1.

(S6: Store Internal Image, Outer Appearance Image, and Timing Information in Association with One Another)

The control unit 41 stores the internal image identified in Step S5, the outer appearance image acquired in Step S4, and the timing information in the storage unit 44 in association with one another. This is the end of the operation relating to the processing for storing the image and the timing information.

Figure 5:
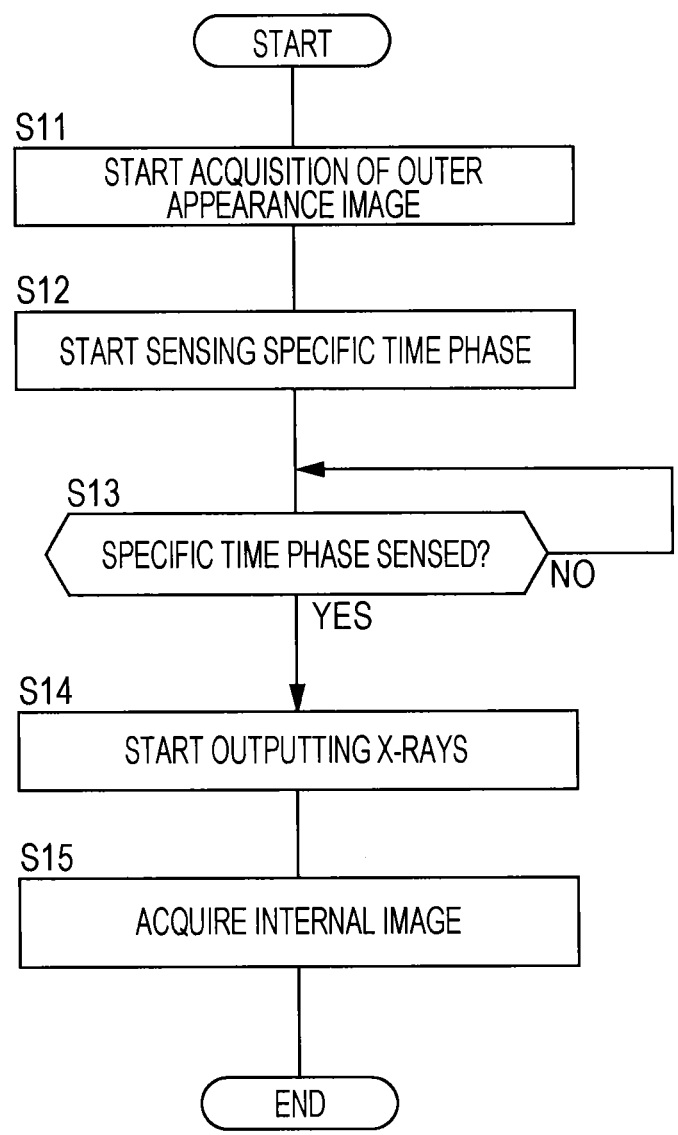
FIG. 5 is a flowchart illustrating the first operation example of the medical image diagnostic apparatus (X-ray CT apparatus) according to the first embodiment.

(Photographing Based on Stored Information: FIG. 5)

(S11: Start Acquisition of Outer Appearance Image)

In response to a predetermined operation for starting the photographing, the outer appearance image acquiring unit 50 starts the acquisition of the outer appearance image of the predetermined body part of the subject E. The predetermined operation may be an operation performed on a photographing start switch of the outer appearance image acquiring unit 50 or may be an operation performed on the operation unit 46 in order to cause the control unit 41 to control the outer appearance image acquiring unit 50 to acquire the outer appearance image. Further, the outer appearance image acquired in this operation example is the images (moving image or a plurality of still images) repeatedly acquired along time series. A repetition rate thereof is determined based on, for example, the speed of the action of the predetermined body part. As a specific example, a relatively low repetition rate is used when the joint is slowly bent, while a relatively high repetition rate is used when the joint is quickly bent.

Note that, along with the start of the acquisition of the outer appearance image, it is possible to control the pedestal driving unit 15 to start rotating the X-ray generating unit 11, the X-ray detecting unit 12, and the like. The X-rays are not output in this stage.

(S12 and S13: Sense Specific Time Phase)

The time phase sensing unit 436 compares each of the outer appearance images (new outer appearance images) repeatedly acquired by the outer appearance image acquiring unit 50 with the outer appearance image stored in the storage unit 44, to thereby sense the arrival of the specific time phase corresponding to the timing information.

(S14: Start Outputting X-Rays)

In response to the fact that the time phase sensing unit 436 has sensed the arrival of the specific time phase, the control unit 41 controls the internal image acquiring unit 100 to start outputting X-rays. Note that, by rotating the X-ray generating unit 11 and the like in advance as described above, CT photographing can be started smoothly.

(S15: Acquire Internal Image)

In response to the start of the outputting of the X-rays performed in Step S14, the internal image acquiring unit 100 starts the acquisition of the internal image. An acquisition time (scan time) for the internal image can be set appropriately based on an exposure dose, a treatment policy, and the like.

The internal image obtained in this operation example is an image that represents the time phase corresponding to the occurrence timing of the biological reaction. Further, according to this operation example, the photographing can be performed at a notable timing, in other words, the occurrence timing of the biological reaction, which can reduce the exposure dose. Further, the photographing can be performed without missing the notable timing.

Second Operation Example

Figure 6:
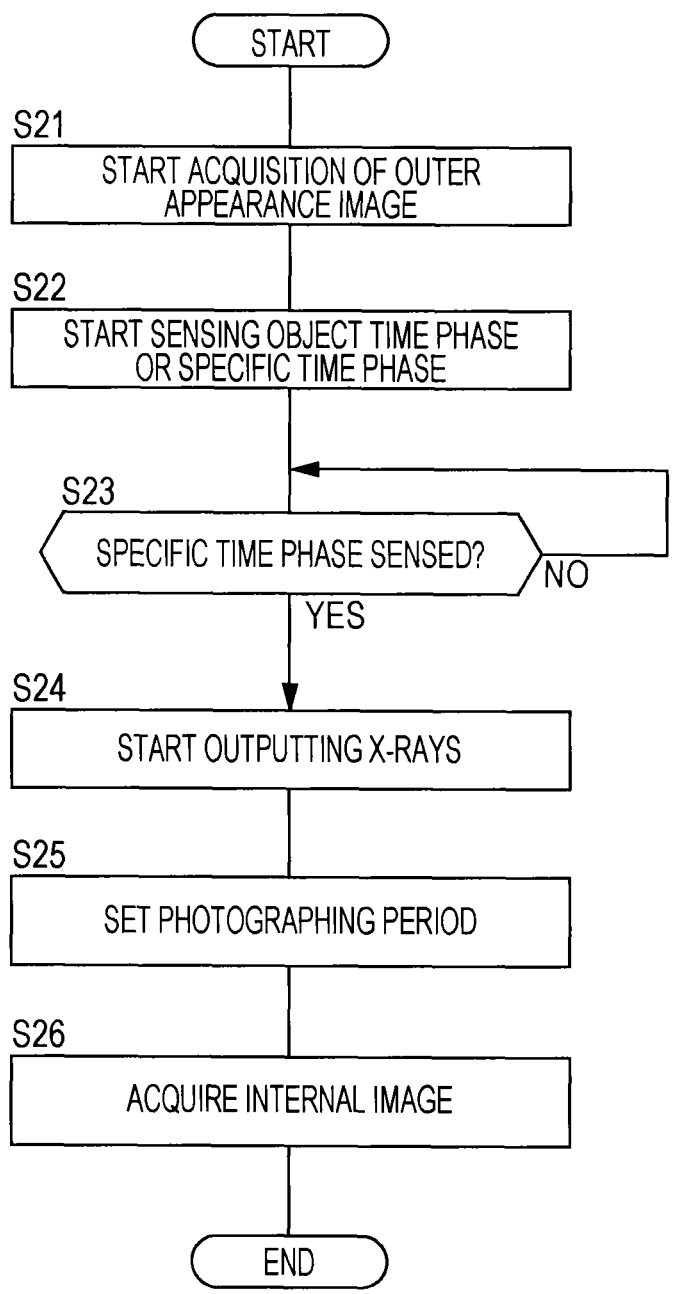
FIG. 6 is a flowchart illustrating a second operation example of the medical image diagnostic apparatus (X-ray CT apparatus) according to the first embodiment.

In this operation example, the photographing is performed during the predetermined period including the time phase corresponding to the occurrence timing of the biological reaction. This operation example also includes the processing for storing the image and the timing information and the photographing based on the stored information, but the former is the same as the first operation example, and hence the description thereof is omitted. An example of the latter is described with reference to FIG. 6.

(S21: Start Acquisition of Outer Appearance Image)

In response to the predetermined operation for starting the photographing, the outer appearance image acquiring unit 50 starts the acquisition of the outer appearance image of the predetermined body part of the subject E. Further, at the start of the acquisition of the outer appearance image, the pedestal driving unit 15 can be controlled to start rotating the X-ray generating unit 11 and the like. The X-rays are not output in this stage. Details of processing of this step are the same as the first operation example.

(S22 and S23: Sense Object Time Phase or Specific Time Phase)

The time phase sensing unit 436 compares each of the outer appearance images (new outer appearance images) repeatedly acquired by the outer appearance image acquiring unit 50 with the outer appearance image stored in the storage unit 44, to thereby sense the arrival of the object time phase included in the predetermined period corresponding to a photographing period or the arrival of the specific time phase corresponding to the timing information. The time phase to be sensed is selected based on the above-mentioned relationship between the specific time phase and the predetermined period.

(S24: Start Outputting X-Rays)

In response to the fact that the time phase sensing unit 436 has sensed the arrival of the object time phase or the specific time phase, the control unit 41 controls the internal image acquiring unit 100 to start outputting X-rays. Note that, by rotating the X-ray generating unit 11 and the like in advance as described above, the CT photographing can be started smoothly.

(S25: Set Photographing Period)

The control unit 41 sets the photographing period in response to the fact that the time phase sensing unit 436 has sensed the object time phase or the specific time phase. This processing is executed by, for example, a timer function of a microprocessor for measuring the time having a length determined in advance. Note that, Steps S24 and S25 are started at substantially the same time. Further, the photographing time can be set appropriately based on the exposure dose, the treatment policy, and the like.

(S26: Acquire Internal Image)

In response to the start of the outputting of the X-rays in Step S24, the internal image acquiring unit 100 starts the acquisition of the internal image. The photographing is continued over the photographing period set in Step S25. In other words, in response to the fact that the photographing time has elapsed, the control unit 41 stops outputting the X-rays.

The internal image obtained in this operation example is an image that represents the action of the predetermined body part performed during the predetermined period including the time phase corresponding to the occurrence timing of the biological reaction. According to this operation example, the photographing can be performed only during the predetermined period including the notable timing, in other words, the occurrence timing of the biological reaction, which can reduce the exposure dose. Further, the photographing can be performed without missing the notable timing.

Third Operation Example

Figure 7:
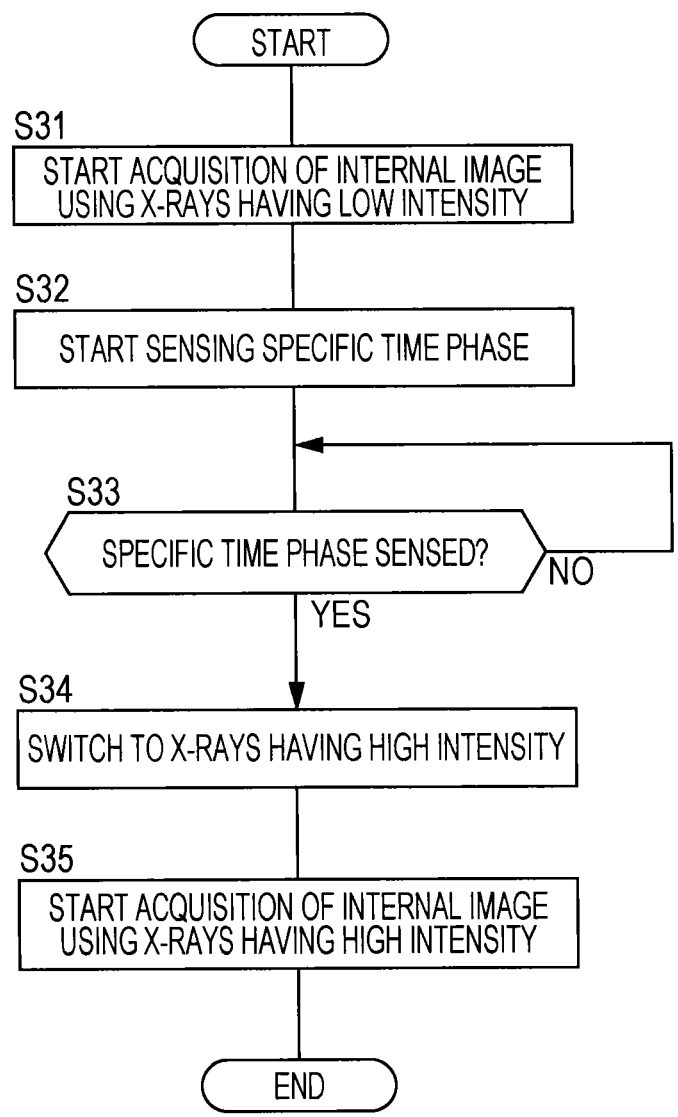
FIG. 7 is a flowchart illustrating a third operation example of the medical image diagnostic apparatus (X-ray CT apparatus) according to the first embodiment.

In this operation example, the photographing is performed by increasing the X-ray intensity in the specific time phase corresponding to the occurrence timing of the biological reaction. This operation example also includes the processing for storing the image and the timing information and the photographing based on the stored information, but the former is the same as the first operation example, and hence the description thereof is omitted. An example of the latter is described with reference to FIG. 7. In the following example, the internal image is used to sense the specific time phase, but in the case of acquiring the outer appearance image in parallel with the internal image, the outer appearance image can be used to sense the specific time phase. Further, the first and second intensities of X-rays are assumed to be determined in advance.

(S31: Start Acquisition of Internal Image Using X-Rays Having Low Intensity)

When a predetermined instruction to start the photographing is issued, the control unit 41 controls the internal image acquiring unit 100 to start the acquisition of the internal image using X-rays having a low intensity (second intensity). This processing is executed in the same manner as the first operation example.

(S32 and S33: Sense Specific Time Phase)

The time phase sensing unit 436 compares each of the outer appearance images (new outer appearance images) repeatedly acquired by the outer appearance image acquiring unit 50 with the outer appearance image stored in the storage unit 44, to thereby sense the arrival of the specific time phase corresponding to the timing information.

(S34: Switch to X-Rays Having High Intensity)

In response to the fact that the time phase sensing unit 436 has sensed the arrival of the specific time phase, the control unit 41 controls the internal image acquiring unit 100 to switch the intensity of the X-rays output from the X-ray generating unit 11 from the low intensity (second intensity) to a high intensity (first intensity).

(S35: Start Acquisition of Internal Image Using X-Rays Having High Intensity)

In response to the switching of the X-ray intensity performed in Step S34, the internal image acquiring unit 100 starts the acquisition of the internal image using the X-rays having the high intensity. The acquisition time (scan time) for the internal image can be set appropriately based on the exposure dose, the treatment policy, and the like.

In response to the fact that the specific time phase has elapsed, the control unit 41 controls the internal image acquiring unit 100 to switch the X-ray intensity from the high intensity to the low intensity. Alternatively, in response to the fact that the specific time phase has elapsed, the control unit 41 controls the internal image acquiring unit 100 to stop outputting the X-rays.

According to this operation example, a relatively high-definition image is acquired by using the X-rays having the high intensity in the time phase corresponding to the occurrence timing of the biological reaction, while in the other time phases, a relatively low-definition image is acquired by using the X-rays having the low intensity. Therefore, while achieving reduction of the exposure dose, it is possible to acquire a high-definition image at the notable timing, in other words, the occurrence timing of the biological reaction.

Fourth Operation Example

Figure 8:
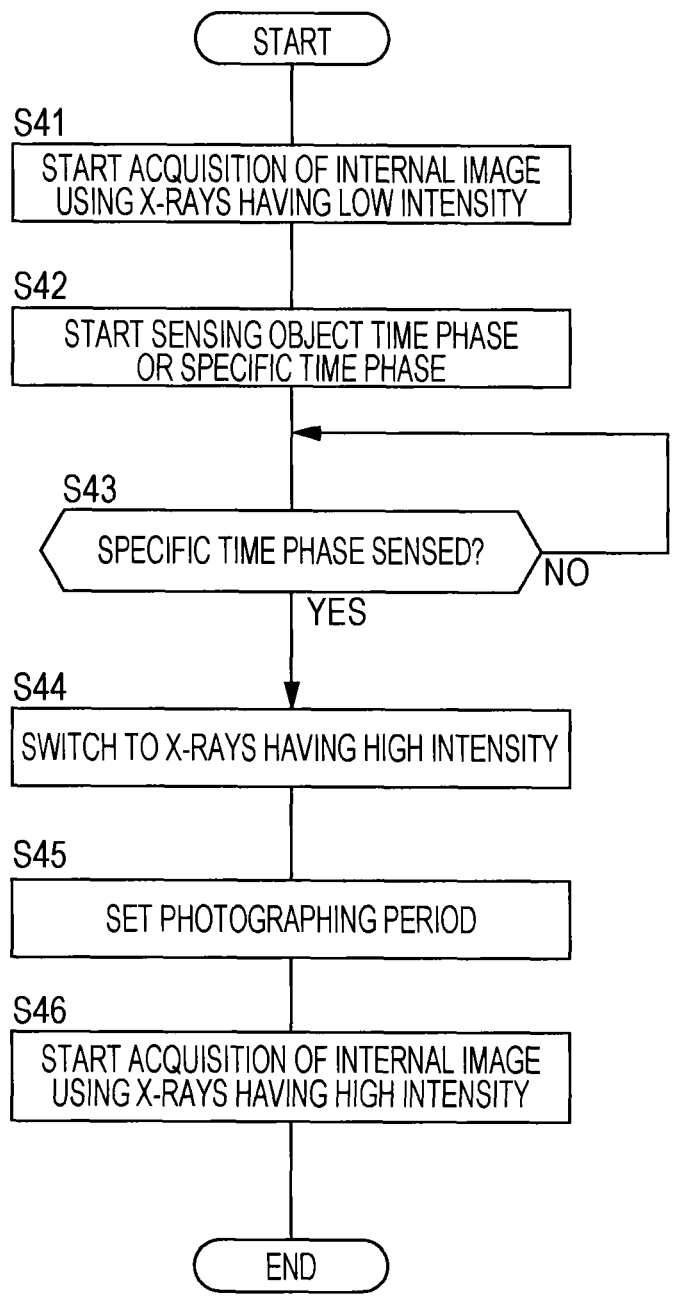
FIG. 8 is a flowchart illustrating a fourth operation example of the medical image diagnostic apparatus (X-ray CT apparatus) according to the first embodiment.

In this operation example, the photographing is performed by increasing the X-ray intensity during the predetermined period including the time phase corresponding to the occurrence timing of the biological reaction. This operation example also includes the processing for storing the image and the timing information and the photographing based on the stored information, but the former is the same as the first operation example, and hence the description thereof is omitted. An example of the latter is described with reference to FIG. 8. In the following example, the internal image is used to sense the specific time phase, but in the case of acquiring the outer appearance image in parallel with the internal image, the outer appearance image can be used to sense the specific time phase. Further, the first and second intensities of X-rays are assumed to be determined in advance.

(S41: Start Acquisition of Internal Image Using X-Rays Having Low Intensity)

When a predetermined instruction to start the photographing is issued, the control unit 41 controls the internal image acquiring unit 100 to start the acquisition of the internal image using X-rays having a low intensity (second intensity). This processing is executed in the same manner as the first operation example.

(S42 and S43: Sense Object Time Phase or Specific Time Phase)

The time phase sensing unit 436 compares each of the outer appearance images (new outer appearance images) repeatedly acquired by the outer appearance image acquiring unit 50 with the outer appearance image stored in the storage unit 44, to thereby sense the arrival of the object time phase included in the predetermined period corresponding to the photographing period or the arrival of the specific time phase corresponding to the timing information. The time phase to be sensed is selected based on the above-mentioned relationship between the specific time phase and the predetermined period.

(S44: Switch to X-Rays Having High Intensity)

In response to the fact that the time phase sensing unit 436 has sensed the object time phase or the specific time phase, the control unit 41 controls the internal image acquiring unit 100 to switch the intensity of the X-rays output from the X-ray generating unit 11 from the low intensity (second intensity) to the high intensity (first intensity).

(S45: Set Photographing Period)

The control unit 41 sets the photographing period in response to the fact that the time phase sensing unit 436 has sensed the object time phase or the specific time phase. This processing is executed in the same manner as the second processing example. Note that, Steps S44 and S45 are started at substantially the same time. Further, the photographing time can be set appropriately based on the exposure dose, the treatment policy, and the like.

(S46: Start Acquisition of Internal Image Using X-Rays Having High Intensity)

In response to the switching of the X-ray intensity performed in Step S44, the internal image acquiring unit 100 starts the acquisition of the internal image using the X-rays having the high intensity. The acquisition time (scan time) for the internal image can be set appropriately based on the exposure dose, the treatment policy, and the like.

In response to the fact that the photographing period has elapsed, the control unit 41 controls the internal image acquiring unit 100 to switch the X-ray intensity from the high intensity to the low intensity. Alternatively, in response to the fact that the photographing period has elapsed, the control unit 41 controls the internal image acquiring unit 100 to stop outputting the X-rays.

According to this operation example, a relatively high-definition image is acquired by using the X-rays having the high intensity in the time phase included in the set photographing period, while in the other time phases, a relatively low-definition image is acquired by using the X-rays having the low intensity. Therefore, while achieving reduction of the exposure dose, it is possible to acquire a high-definition image at the notable timing, in other words, the predetermined period including the occurrence timing of the biological reaction.

Fifth Operation Example

FIG. 15

(S111: Acquire Internal Image)

In the same manner as the first operation example, the acquisition of the plurality of internal images different in time phase is started.

(S112: Acquire Outer Appearance Image)

The outer appearance image acquiring unit 50 starts the moving image photographing for the predetermined body part of the subject E. Accordingly, the plurality of outer appearance images along time series are obtained. The acquisition of the outer appearance image is continued until at least the input of the occurrence information on the biological reaction (S114).

(S113 and S114: Input Occurrence Information on Biological Reaction)

When recognizing the occurrence of the predetermined biological reaction (S113: YES), the operator operates the operation unit 46. The operation unit 46 that has received the operation inputs the signal serving as the occurrence information on the biological reaction to the control unit 41 (S114).

(S115: Identify Internal Image)

The image identifying unit 434 identifies the internal image acquired at substantially the same time as the input of the occurrence information on the biological reaction (S114) among the plurality of internal images acquired in Step S111.

(S116: Identify Outer Appearance Image)

In addition, the image identifying unit 434 identifies the outer appearance image acquired at substantially the same time as the input of the occurrence information on the biological reaction (S114) among the plurality of outer appearance images acquired in Step S112. Note that, the processing for identifying the internal image and the processing for identifying the outer appearance image may be performed in any order or may be performed in parallel.

(S117: Store Internal Image and Outer Appearance Image in Association with Each Another)

The control unit 41 stores the internal image identified in Step S115 and the outer appearance image identified in Step S116 in the storage unit 44 in association with each another. This is the end of the operation relating to the second operation example.

(Display Mode)

A method of displaying the internal image and the outer appearance image stored as described above is described. Display modes described below can also be applied appropriately to a second embodiment.

First Display Example

This display example relates to a case where both the internal image and the outer appearance image are displayed.

In response to the reception of a predetermined trigger, the control unit 41 reads the internal image and the outer appearance image that are associated with each other from the storage unit 44, and displays the internal image and the outer appearance image on the display unit 45. In a display mode therefor, only one of the internal image and the outer appearance image that have been read may be displayed, or both thereof may be displayed. The latter includes a case where both the images are displayed side by side and a case where both the images are displayed with one superimposed on the other.

According to the first display example, both the images that are associated with each other can easily be viewed while being compared with each other.

Second Display Example

This display example relates to a case where there is a request to display one of the internal image and the outer appearance image. In a case of employing this display example, the operation unit 46 is used to issue an instruction to display one of the internal image and the outer appearance image that are associated with each other.

The control unit 41 displays a screen for designating the image on the display unit 45. This screen presents, for example, at least one piece of information including patient identification information (such as patient's ID and patient name), a photographing date/time, and a reduced image (thumbnail) of the photographed image. The operator uses the operation unit 46 to designate a desired piece of the presented information.

The control unit 41 recognizes a designation result thereof as the instruction to display one of the above-mentioned images, and in response to the instruction, displays the designated image and the image associated therewith (corresponding to the other one of the above-mentioned images) on the display unit 45.

According to the second display example, it is possible to facilitate work for viewing both the images that are associated with each other.

Third Display Example

This display example relates to a case of subjecting the internal image to moving image display (including slide-show-type display).

The control unit 41 stores the plurality of internal images acquired by the internal image acquiring unit 100 in the storage unit 44. Then, the control unit 41 executes the moving image display by switching and displaying those internal images along time series at predetermined time intervals on the display unit 45.

When performing such moving image display, the control unit 41 displays the information indicating the occurrence of the biological reaction on the display unit 45 at a timing at which the internal image (at least one frame; referred to as "specific frame") identified by the image identifying unit 434 is displayed. The displayed information is referred to as "occurrence timing information". Examples of the occurrence timing information include the character string information or the image information indicating the occurrence of the biological reaction and numerical value information indicating the occurrence timing of the biological reaction or an occurrence period (duration).

Examples of the timing for displaying the occurrence timing information include the same timing as the displaying of (the first one of) the specific frames, the same timing as the displaying of any one of a plurality of specific frames, and a timing before the displaying of (the first one of) the specific frames. In the case of performing the displaying before the specific frame, it is possible to display information for counting down to the arrival of a display timing for (the first one of) the specific frames. Further, information for counting up with the occurrence of the start of the biological reaction as a trigger or information for counting down to the end of the biological reaction may be displayed.

According to the third display example, it is possible to easily realize which state of inside of the subject causes occurrence of the biological reaction.

(Action/Effects)

Action and effects of the X-ray CT apparatus 1 according to this embodiment are described.

An example of the X-ray CT apparatus 1 includes the internal image acquiring unit 100, the operation unit 46, the outer appearance image acquiring unit 50, the storage unit 44, the image identifying unit 434, and the control unit 41. The internal image acquiring unit 100 continuously or intermittently irradiates the predetermined body part of the subject E with X-rays to acquire the plurality of internal images different in time phase. The operation unit 46 (input unit) inputs the occurrence information indicating the occurrence of the predetermined biological reaction of the subject E. The outer appearance image acquiring unit 50 acquires the outer appearance image by photographing the predetermined body part at least at the photographing timing corresponding to the input of the occurrence information. The image identifying unit 434 (identification unit) identifies the internal image acquired at substantially the same time as the input of the occurrence information among the plurality of internal images. The control unit 41 stores the identified internal image and the outer appearance image acquired at the above-mentioned photographing timing in the storage unit 44 in association with each other.

The X-ray CT apparatus 1 is thus configured to store the internal image and the outer appearance image that are obtained at a timing corresponding to the occurrence of the biological reaction in association with each other. Therefore, a viewer of the image can recognize that the internal image (and the outer appearance image) is obtained at the occurrence timing of the biological reaction. Further, based on the internal image, the viewer can grasp an internal state at the occurrence timing of the biological reaction, in other words, the action state of the body. Therefore, according to the X-ray CT apparatus 1, a relationship between the action state of the body and the occurrence timing of the biological reaction can be grasped. For example, in a case of performing an examination of the joint part, the viewer can grasp which state the bones within the joint are in when the pain occurs.

Another example of the X-ray CT apparatus 1 includes the internal image acquiring unit 100, the operation unit 46, the outer appearance image acquiring unit 50, the storage unit 44, and the control unit 41. The internal image acquiring unit 100 continuously or intermittently irradiates the predetermined body part of the subject E with X-rays to acquire the plurality of internal images different in time phase. The operation unit 46 is used to input the occurrence information indicating the occurrence of the predetermined biological reaction of the subject E. The outer appearance image acquiring unit 50 acquires the outer appearance image by photographing the predetermined body part of the subject E at least at the photographing timing corresponding to the input of the occurrence information. The control unit 41 stores the outer appearance image acquired at the photographing timing and the timing information indicating the occurrence timing of the biological reaction in the storage unit 44 in association with each other, and stores at least one of the plurality of internal images acquired by the internal image acquiring unit 100 in the storage unit 44.

The X-ray CT apparatus 1 may include the image identifying unit 434. The image identifying unit 434 identifies the internal image acquired at substantially the same time as the input of the occurrence information among the plurality of internal images acquired by the internal image acquiring unit 100. The control unit 41 stores the identified internal image, the outer appearance image acquired at the above-mentioned photographing timing, and the timing information in the storage unit 44 in association with one another.

In a case where the outer appearance image acquiring unit 50 repeatedly photographs the predetermined body part to sequentially acquire the outer appearance images, the image identifying unit 434 may be configured to identify the outer appearance image acquired at substantially the same time as the input of the occurrence information among the sequentially-acquired outer appearance images. The control unit 41 stores the identified outer appearance image as the outer appearance image acquired at the above-mentioned photographing timing in the storage unit 44 in association with the timing information.

The X-ray CT apparatus 1 may include the time phase sensing unit 436. The time phase sensing unit 436 senses the arrival of the specific time phase or the object time phase by comparing the new internal image acquired by applying the X-rays having the second intensity that is relatively low or the new outer appearance image acquired by the outer appearance image acquiring unit 50 with the outer appearance image stored in the storage unit 44. In response to the arrival of the time phase, the control unit 41 acquires the new internal image or switches the X-ray intensity.

According to the X-ray CT apparatus 1 described above, the outer appearance image acquired at the photographing timing corresponding to the input of the occurrence information indicating the occurrence timing of the biological reaction and the timing information indicating the occurrence timing of the biological reaction can be stored in the storage unit 44 in association with each other, and the internal image can also be stored in the storage unit 44. Therefore, the viewer of the image can recognize that the outer appearance image is obtained at the occurrence timing of the biological reaction.

Further, by storing the internal image acquired at substantially the same time as the input of the occurrence information as well in association with the outer appearance image and the timing information, it is possible to recognize that the internal image is obtained at the occurrence timing of the biological reaction. In addition, based on the internal image, the viewer can grasp the internal state at the occurrence timing of the biological reaction, in other words, the action state of the body.

Therefore, according to the X-ray CT apparatus 1, it is possible to grasp the relationship between the action state of the body and the occurrence timing of the biological reaction. For example, in the case of performing the examination of the joint part, the viewer can grasp which state the bones within the joint are in when the pain occurs.

Further, it is possible to reduce the exposure dose by using the outer appearance image stored in the storage unit 44 to perform new photographing.

Second Embodiment

In the first embodiment, the outer appearance image and the timing information are stored in association with each other, while in the second embodiment, the internal image and the timing information are stored in association with each other. In this embodiment, there is no need to provide the outer appearance image acquiring unit.

(Configuration)

Figure 9:
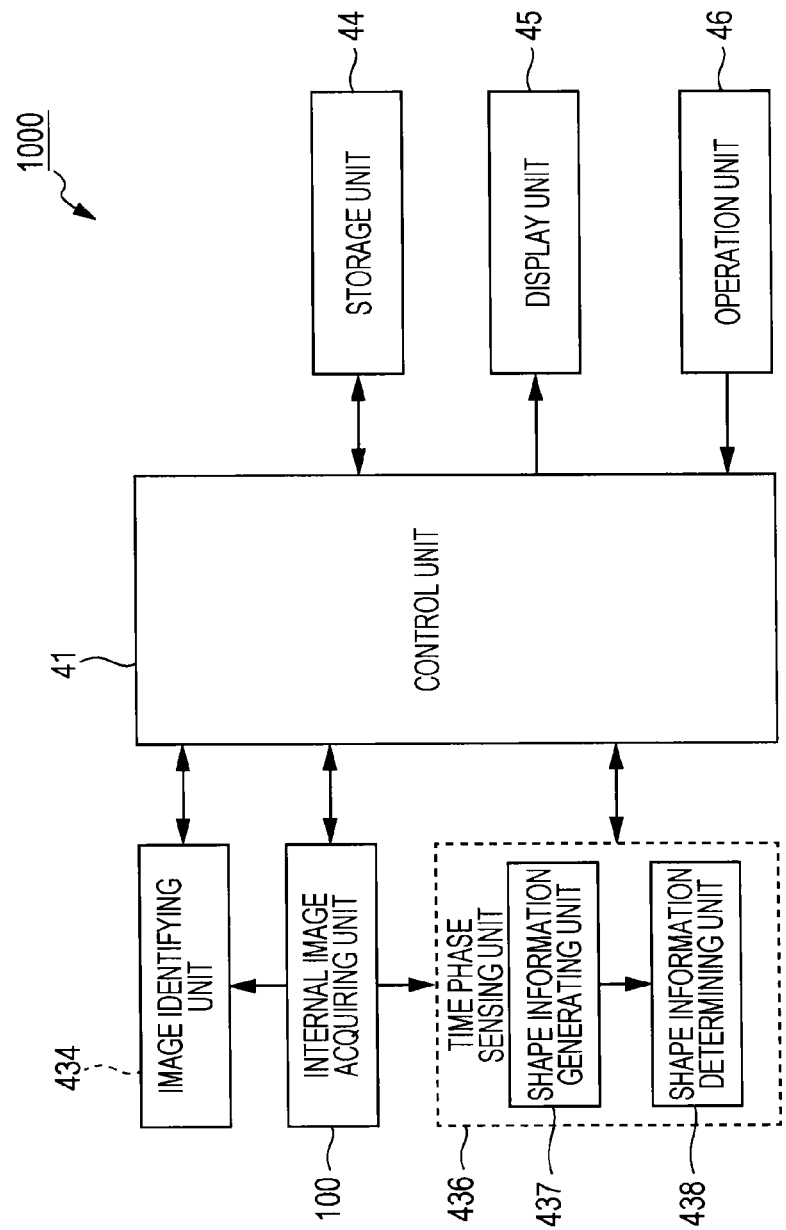
FIG. 9 is a block diagram illustrating a configuration of a medical image diagnostic apparatus (X-ray CT apparatus) according to a second embodiment.

FIG. 9 illustrates a configuration example of a medical image diagnostic apparatus (X-ray CT apparatus) 1000 according to this embodiment. FIG. 9 corresponds to FIG. 2 of the first embodiment. A detailed configuration of the X-ray CT apparatus 1000 conforms to, for example, FIG. 1.

The X-ray CT apparatus 1000 includes the control unit 41, the storage unit 44, the display unit 45, the operation unit 46, the internal image acquiring unit 100, the image identifying unit 434, and the time phase sensing unit 436. The time phase sensing unit 436 includes the shape information generating unit 437 and the shape information determining unit 438. Each of those components has the same configuration and function as the corresponding component in the first embodiment. The X-ray CT apparatus 1000 is now described in consideration of what is described in the first embodiment. The same reference numerals as those of the first embodiment are used.

The internal image acquiring unit 100 continuously or intermittently irradiates the predetermined body part of the subject E with X-rays to acquire the plurality of internal images different in time phase. The operation unit 46 is used to input the occurrence information indicating the occurrence of the predetermined biological reaction of the subject E. The image identifying unit 434 identifies the internal image acquired at substantially the same time as the input of the occurrence information among the plurality of internal images acquired by the internal image acquiring unit 100. The control unit 41 stores the internal image identified by the image identifying unit 434 and the timing information indicating the occurrence timing of the biological reaction in the storage unit 44 in association with each other.

The internal image acquiring unit 100 may be configured to acquire the new internal image based on the internal image and the timing information stored in the storage unit 44. With regard to this case, two processing examples are described.

In a first processing example, based on the internal image and the timing information stored in the storage unit 44, the internal image acquiring unit 100 acquires the new internal image in the specific time phase corresponding to the timing information. The specific time phase has been described in the first embodiment.

Further, in the first processing example, the internal image acquiring unit 100 can acquire the plurality of new internal images by applying the X-rays having the first intensity in the specific time phase and applying the X-rays having the second intensity that is lower than the first intensity in the time phase other than the specific time phase. In other words, the photographing can be performed by using the X-rays having a relatively high intensity in the specific time phase, while in the time phase other than the specific time phase, the photographing can be performed by using the X-rays having a relatively low intensity.

Further, in the first processing example, the time phase sensing unit 436 senses the arrival of the specific time phase by comparing the new internal image acquired by applying the X-rays having the second intensity with the internal image stored in the storage unit 44. Note that, in the first embodiment, the new internal image or the new outer appearance image is compared with the outer appearance image stored in the storage unit 44, but in this embodiment, the internal images are compared with each other. The first and second embodiments are different only in the type of image, and hence the comparison processing according to this embodiment can be executed in the same manner as the first embodiment.

A configuration example of the time phase sensing unit 436 includes the shape information generating unit 437 and the shape information determining unit 438. The shape information generating unit 437 analyzes each of the new internal image acquired by applying the X-rays having the second intensity and the internal image stored in the storage unit 44, and generates the predetermined body part shape information indicating the shape of the predetermined body part of the subject E. The shape information determining unit 438 determines whether or not the predetermined body part shape information generated from the new internal image and the predetermined body part shape information generated from the internal image stored in the storage unit 44 substantially match each other. The time phase sensing unit 436 determines that the specific time phase has arrived when it is determined that the above-mentioned pieces of predetermined body part shape information substantially match each other.

When the time phase sensing unit 436 senses the arrival of the specific time phase, the control unit 41 controls the internal image acquiring unit 100 to switch the intensity of the X-rays output from the X-ray generating unit 11 from the second intensity to the first intensity. This is the end of the description of the first processing example.

In a second processing example, based on the internal image and the timing information stored in the storage unit 44, the internal image acquiring unit 100 acquires the new internal image during the predetermined period including the time phase corresponding to the timing information. The predetermined period has been described in the first embodiment.

Further, in the second operation example, the internal image acquiring unit 100 can acquire the plurality of new internal images by applying the X-rays having the first intensity in the time phase included in the predetermined period and applying the X-rays having the second intensity that is lower than the first intensity in the time phase other than the predetermined period. In other words, the photographing can be performed by using the X-rays having a relatively high intensity in the time phase included in the predetermined period, while in the time phase other than the predetermined period, the photographing can be performed by using the X-rays having a relatively low intensity.

Further, in the second operation example, the time phase sensing unit 436 compares the new internal image acquired by applying the X-rays having the second intensity with the internal image stored in the storage unit 44, to thereby sense the arrival of the time phase included in the predetermined period. This processing and the configuration for execution thereof are the same as those of the first embodiment and the above-mentioned first processing example. When the time phase sensing unit 436 senses the arrival of the time phase included in the predetermined period, the control unit 41 controls the internal image acquiring unit 100 to switch the intensity of the X-rays output from the X-ray generating unit 11 from the second intensity to the first intensity. This is the end of the description of the second processing example.

The image identifying unit 434 is described. In the first embodiment, the description has been made of the three processing examples, two of which use the outer appearance image (analysis unit 435). In this embodiment, the outer appearance image is not used, and hence those two processing examples cannot be applied thereto. Note that, in a case where the outer appearance image acquiring unit is added to the configuration of this embodiment, all the three processing examples can be applied in the same manner as the first embodiment.

The first input timing information indicating an input timing for the occurrence information using the operation unit 46 and the second input timing information indicating the timing at which the internal image is acquired by the internal image acquiring unit 100 are input to the image identifying unit 434. The image identifying unit 434 identifies the internal image corresponding to the second input timing information received at substantially the same time as the first input timing information. In other words, the image identifying unit 434 monitors both the input timing for the occurrence information and the acquisition timing for the internal image, and identifies the internal image acquired at a timing that substantially match with the input timing. The identified internal image is set as the internal image acquired at substantially the same time as the input of the occurrence information among the plurality of internal images acquired by the internal image acquiring unit 100.

(Operation)

An operation of the X-ray CT apparatus 1000 according to this embodiment is described. First and second operation examples are described below. In the first operation example, the photographing is performed by increasing the X-ray intensity in the time phase corresponding to the occurrence timing of the biological reaction. In the second operation example, the photographing is performed by increasing the X-ray intensity during the predetermined period including the time phase corresponding to the occurrence timing of the biological reaction.

First Operation Example

Figure 10:
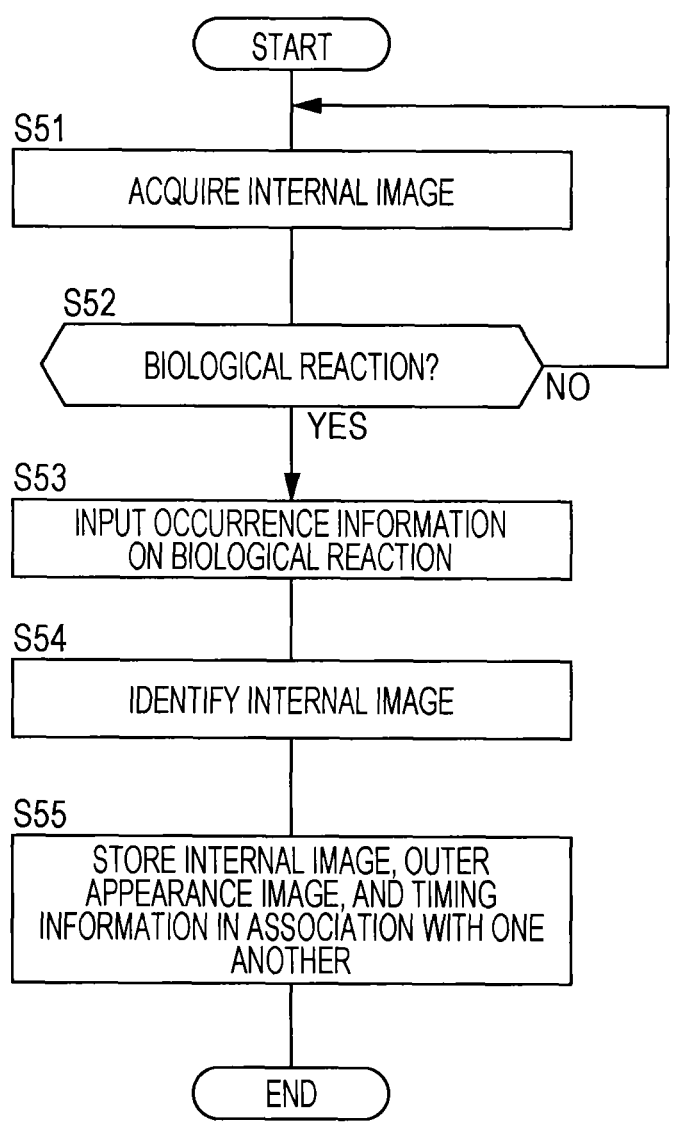
FIG. 10 is a flowchart illustrating a first operation example of the medical image diagnostic apparatus (X-ray CT apparatus) according to the second embodiment.

In this operation example, the photographing is performed by increasing the X-ray intensity in the time phase corresponding to the occurrence timing of the biological reaction. In the following, processing for storing the internal image and the timing information is first described with reference to FIG. 10, and then the photographing based on the stored information is described with reference to FIG. 11. Note that, the former processing and the latter processing can be continuously performed (preliminary photographing and regular photographing) or can be performed on different dates/times.

(Storage of Internal Image and Timing Information: FIG. 4)

(S51: Acquire Internal Image)

The acquisition of the plurality of internal images different in time phase is started. The acquisition of the internal image is continued until at least the input of the occurrence information on the biological reaction (S53). Processing for acquiring the internal image is performed in the same manner as the first embodiment.

(S52 and S53: Input Occurrence Information on Biological Reaction)

When recognizing the occurrence of a predetermined biological reaction (S52: YES), the operator operates the operation unit 46. The operation unit 46 that has received the operation inputs the signal serving as the occurrence information on the biological reaction to the control unit 41 (S53).

(S54: Identify Internal Image)

It is assumed that the first input timing information indicating the input timing for the occurrence information and the second input timing information indicating the timing at which the internal image is acquired by the internal image acquiring unit 100 are input to the image identifying unit 434. The image identifying unit 434 identifies the internal image corresponding to the second input timing information received at substantially the same time as the first input timing information corresponding to Step S53.

(S55: Store Internal Image and Timing Information in Association with Each Another)

The control unit 41 stores the internal image identified in Step S54 and the timing information in the storage unit 44 in association with each another. This is the end of the operation relating to the processing for storing the image and the timing information.

Figure 11:
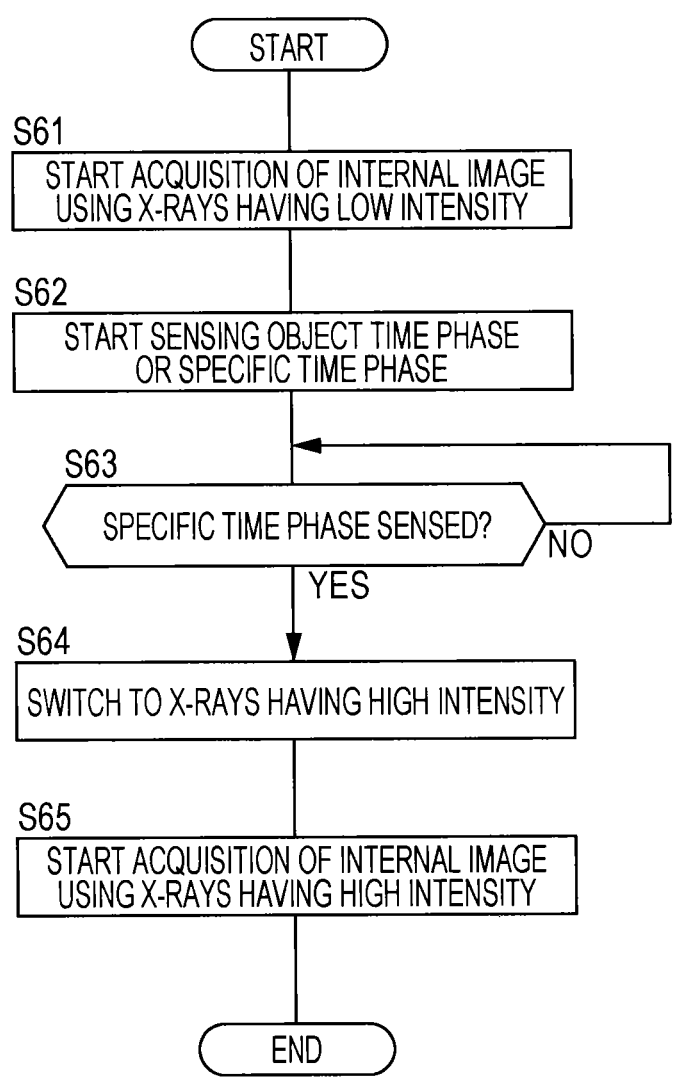
FIG. 11 is a flowchart illustrating the first operation example of the medical image diagnostic apparatus (X-ray CT apparatus) according to the second embodiment.

(Photographing Based on Stored Information: FIG. 11)

(S61: Start Acquisition of Internal Image Using X-Rays Having Low Intensity)

When a predetermined instruction to start the photographing is issued, the control unit 41 controls the internal image acquiring unit 100 to start the acquisition of the internal image using X-rays having a low intensity (second intensity). This processing is executed in the same manner as the first embodiment. Note that, the first and second intensities of X-rays are assumed to be determined in advance.

(S62 and S63: Sense Specific Time Phase)

The time phase sensing unit 436 compares each of the internal images (new internal images) repeatedly acquired by using the X-rays having the low intensity with the internal image stored in the storage unit 44, to thereby sense the arrival of the specific time phase corresponding to the timing information.

(S64: Switch to X-Rays Having High Intensity)

In response to the fact that the time phase sensing unit 436 has sensed the arrival of the specific time phase, the control unit 41 controls the internal image acquiring unit 100 to switch the intensity of the X-rays output from the X-ray generating unit 11 from the low intensity (second intensity) to the high intensity (first intensity).

(S65: Start Acquisition of Internal Image Using X-Rays Having High Intensity)

In response to the switching of the X-ray intensity performed in Step S64, the internal image acquiring unit 100 starts the acquisition of the internal image using the X-rays having the high intensity. The acquisition time (scan time) for the internal image can be set appropriately based on the exposure dose, the treatment policy, and the like.

In response to the fact that the specific time phase has elapsed, the control unit 41 controls the internal image acquiring unit 100 to switch the X-ray intensity from the high intensity to the low intensity. Alternatively, in response to the fact that the specific time phase has elapsed, the control unit 41 controls the internal image acquiring unit 100 to stop outputting the X-rays.

According to this operation example, a relatively high-definition image is acquired by using the X-rays having the high intensity in the time phase corresponding to the occurrence timing of the biological reaction, while in the other time phases, a relatively low-definition image is acquired by using the X-rays having the low intensity. Therefore, while achieving reduction of the exposure dose, it is possible to acquire a high-definition image at the notable timing, in other words, the occurrence timing of the biological reaction.

Second Operation Example

Figure 12:
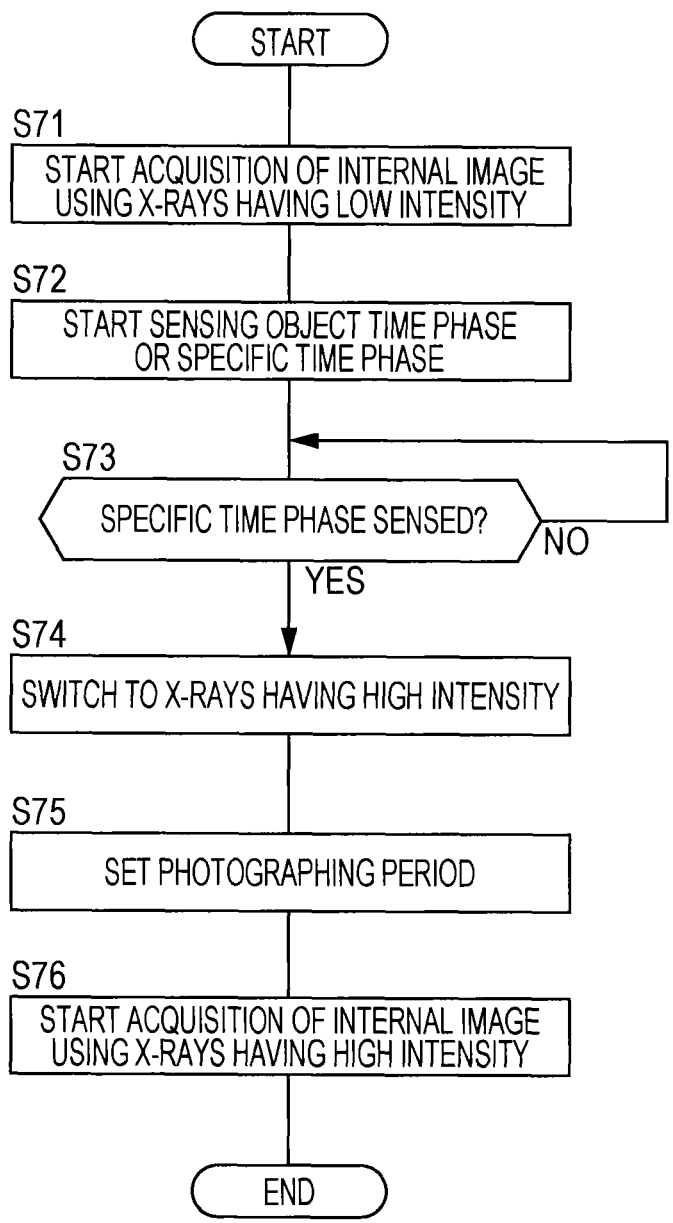
FIG. 12 is a flowchart illustrating a second operation example of the medical image diagnostic apparatus (X-ray CT apparatus) according to the second embodiment.

In this operation example, the photographing is performed by increasing the X-ray intensity during the predetermined period including the time phase corresponding to the occurrence timing of the biological reaction. This operation example also includes the processing for storing the image and the timing information and the photographing based on the stored information, but the former is the same as the first operation example, and hence the description thereof is omitted. An example of the latter is described with reference to FIG. 12. Note that, the first and second intensities of X-rays are assumed to be determined in advance.

(S71: Start Acquisition of Internal Image Using X-Rays Having Low Intensity)

When a predetermined instruction to start the photographing is issued, the control unit 41 controls the internal image acquiring unit 100 to start the acquisition of the internal image using X-rays having the low intensity (second intensity). This processing is executed in the same manner as the first operation example.

(S72 and S73: Sense Object Time Phase or Specific Time Phase)

The time phase sensing unit 436 compares each of the internal images (new internal images) repeatedly acquired by using the X-rays having the low intensity with the internal image stored in the storage unit 44, to thereby sense the arrival of the object time phase included in the predetermined period corresponding to the photographing period or the arrival of the specific time phase corresponding to the timing information. The time phase to be sensed is selected based on the relationship between the specific time phase and the predetermined period, which has been described in the first embodiment.

(S74: Switch to X-Rays Having High Intensity)

In response to the fact that the time phase sensing unit 436 has sensed the object time phase or the specific time phase, the control unit 41 controls the internal image acquiring unit 100 to switch the intensity of the X-rays output from the X-ray generating unit 11 from the low intensity (second intensity) to the high intensity (first intensity).

(S75: Set Photographing Period)

The control unit 41 sets the photographing period in response to the fact that the time phase sensing unit 436 has sensed the object time phase or the specific time phase. This processing is executed in the same manner as the first embodiment. Note that, Steps S74 and S75 are started at substantially the same time. Further, the photographing time can be set appropriately based on the exposure dose, the treatment policy, and the like.

(S76: Start Acquisition of Internal Image Using X-Rays Having High Intensity)

In response to the switching of the X-ray intensity performed in Step S74, the internal image acquiring unit 100 starts the acquisition of the internal image using the X-rays having the high intensity. The acquisition time (scan time) for the internal image can be set appropriately based on the exposure dose, the treatment policy, and the like.

In response to the fact that the photographing period has elapsed, the control unit 41 controls the internal image acquiring unit 100 to switch the X-ray intensity from the high intensity to the low intensity. Alternatively, in response to the fact that the photographing period has elapsed, the control unit 41 controls the internal image acquiring unit 100 to stop outputting the X-rays.

According to this operation example, a relatively high-definition image is acquired by using the X-rays having the high intensity in the time phase included in the set photographing period, while in the other time phases, a relatively low-definition image is acquired by using the X-rays having the low intensity. Therefore, while achieving reduction of the exposure dose, it is possible to acquire a high-definition image at the notable timing, in other words, the predetermined period including the occurrence timing of the biological reaction.

(Action/Effects)

According to the X-ray CT apparatus 1000 of this embodiment, it is possible to store the internal image acquired at substantially the same time as the occurrence of the biological reaction and the timing information indicating the occurrence timing of the biological reaction in association with each other. Therefore, the viewer of the image can recognize that the internal image is obtained at the occurrence timing of the biological reaction. In addition, based on the internal image, the viewer can grasp the internal state at the occurrence timing of the biological reaction, in other words, the action state of the body. Therefore, according to the X-ray CT apparatus 1000, it is possible to grasp the relationship between the action state of the body and the occurrence timing of the biological reaction.

Further, it is possible to reduce the exposure dose by using the internal image stored in the storage unit 44 to perform new photographing.

Modified Examples

A description is made of a medical image diagnostic apparatus according to modified examples of the embodiments. The contents described above in the embodiments can be arbitrarily combined with each of the modified examples. Further, the modified examples can be combined with one another. In the following, the same components as those of the above-mentioned embodiments are denoted by the same reference numerals in the description.

First Modified Example

Figure 13:
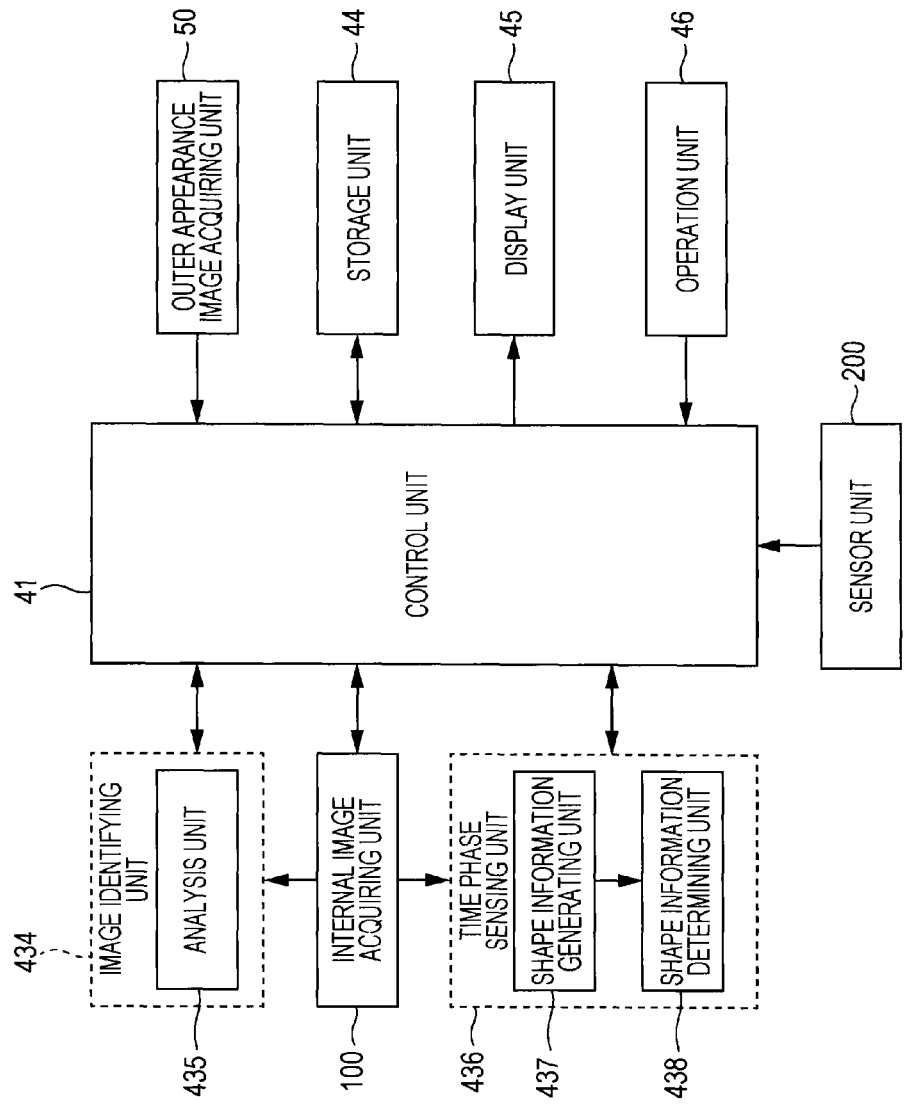
FIG. 13 is a block diagram illustrating a configuration of a medical image diagnostic apparatus according to a first modified example.
Figure 14:
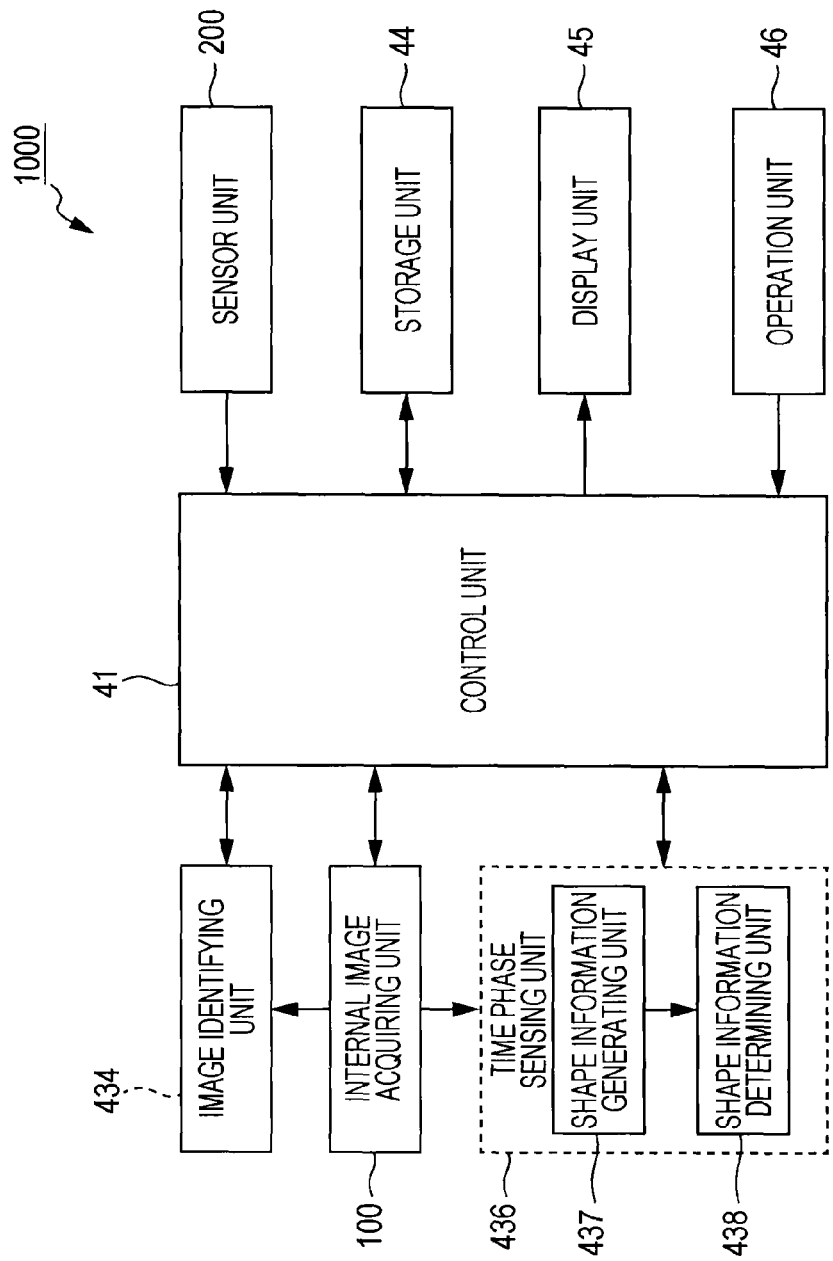
FIG. 14 is a block diagram illustrating the configuration of the medical image diagnostic apparatus according to the first modified example.
Figure 15:
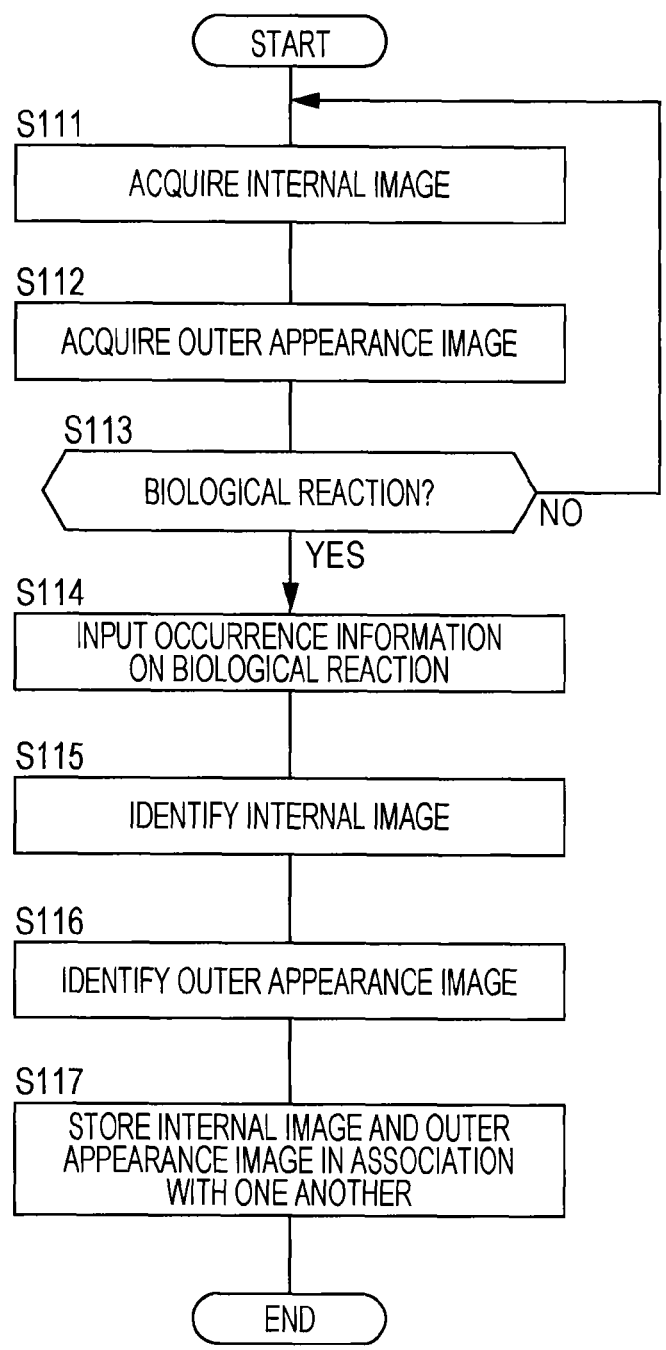
FIG. 15 is a flowchart illustrating a fifth operation example of the medical image diagnostic apparatus (X-ray CT apparatus) according to the first embodiment.

In the above-mentioned embodiments, the operator uses the operation unit 46 to input the fact that the biological reaction has occurred. On the other hand, in a first modified example, the state of the subject E is monitored to automatically sense the occurrence of the biological reaction. FIGS. 13 and 14 illustrate a configuration example of a medical image diagnostic apparatus according to this modified example. FIG. 13 illustrates a case where this modified example is applied to the first embodiment illustrated in FIG. 2. FIG. 14 illustrates a case where this modified example is applied to the second embodiment illustrated in FIG. 9. The medical image diagnostic apparatus according to this modified example is obtained by adding a sensor unit 200 to the above-mentioned embodiments.

The sensor unit 200 monitors the state of the subject E and senses the occurrence of the biological reaction, to thereby input the signal serving as the occurrence information on the biological information. Examples of the biological information to be input include the utterance, the facial expression, the respiration, the perspiration, the electrocardiogram, the blood pressure, the electromyogram, the electroencephalogram, and the pupil diameter. The biological reaction to be sensed is, for example, a change in the biological information accompanied by the pain. Such a biological reaction is known.

The utterance can be sensed by using a microphone. Examples of contents sensed at this time include contents of the utterance and a voice volume.

The contents of the utterance can be sensed by, for example, the microprocessor (not shown) provided to the sensor unit 200 executing a known speech recognition technology. The microprocessor analyzes an electric signal output from the microphone to determine whether or not a content stored in advance has been uttered. When it is determined that the content has been uttered, the microprocessor inputs an occurrence signal to the control unit 41.

The voice volume can be sensed by, for example, the microprocessor (not shown) provided to the sensor unit 200 analyzing the electric signal output from the microphone. The microprocessor determines based on the electric signal whether or not a volume thereof is equal to or larger than a predetermined threshold value. When it is determined that the volume is equal to or larger than the threshold value, the microprocessor inputs the occurrence signal to the control unit 41.

The facial expression and the pupil diameter can be sensed by photographing a face and an eye of the patient and analyzing the photographed images.

The facial expression can be sensed by the microprocessor (not shown) provided to the sensor unit 200 identifying feature points of the facial expression (for example, points indicating characteristic changes of muscles of facial expression accompanied by the occurrence of the pain) stored in advance by analyzing the photographic image and determining whether or not the positional relationship between those feature points matches the positional relationship corresponding to the biological reaction. When it is determined that the positional relationship between those feature points matches the positional relationship corresponding to the biological reaction, the microprocessor inputs the occurrence signal to the control unit 41.

The pupil diameter can be sensed by the microprocessor (not shown) provided to the sensor unit 200 analyzing the photographed image to extract the image area (eye area) corresponding to the eye, analyzing the eye area to identify the image area (pupil area) corresponding to the pupil, and calculating a diameter of the pupil area. The microprocessor determines whether or not the pupil diameter is within a predetermined allowable range. When it is determined that the pupil diameter is out of the predetermined allowable range, the microprocessor inputs the occurrence signal to the control unit 41.

The respiration, the perspiration, the electrocardiogram, the blood pressure, the electromyogram, and the electroencephalogram can be sensed by using publicly-known devices, in other words, a respiration monitoring device, a perspiration monitoring device, an electrocardiograph, a sphygmomanometer, an electromyograph, and an electroencephalograph, respectively. The electric signal indicating detection results obtained by those devices is input to the microprocessor (not shown) provided to the sensor unit 200. The microprocessor determines whether or not the biological reaction has occurred by comparing the detection results with a predetermined threshold value. When it is determined that the biological reaction has occurred, the microprocessor inputs the occurrence signal to the control unit 41.

The medical image diagnostic apparatus that has received an input of the occurrence signal from the sensor unit 200 identifies at least one of the internal image and the outer appearance image acquired at substantially the same time as the input timing thereof. Further, in response to the input of the occurrence signal received from the sensor unit 200, it is possible to change a manner in which at least one of the internal image and the outer appearance image is acquired. For example, in response to the input of the occurrence signal received from the sensor unit 200, it is possible to start acquiring at least one of the internal image and the outer appearance image or switching the X-ray intensity.

Figure 16:
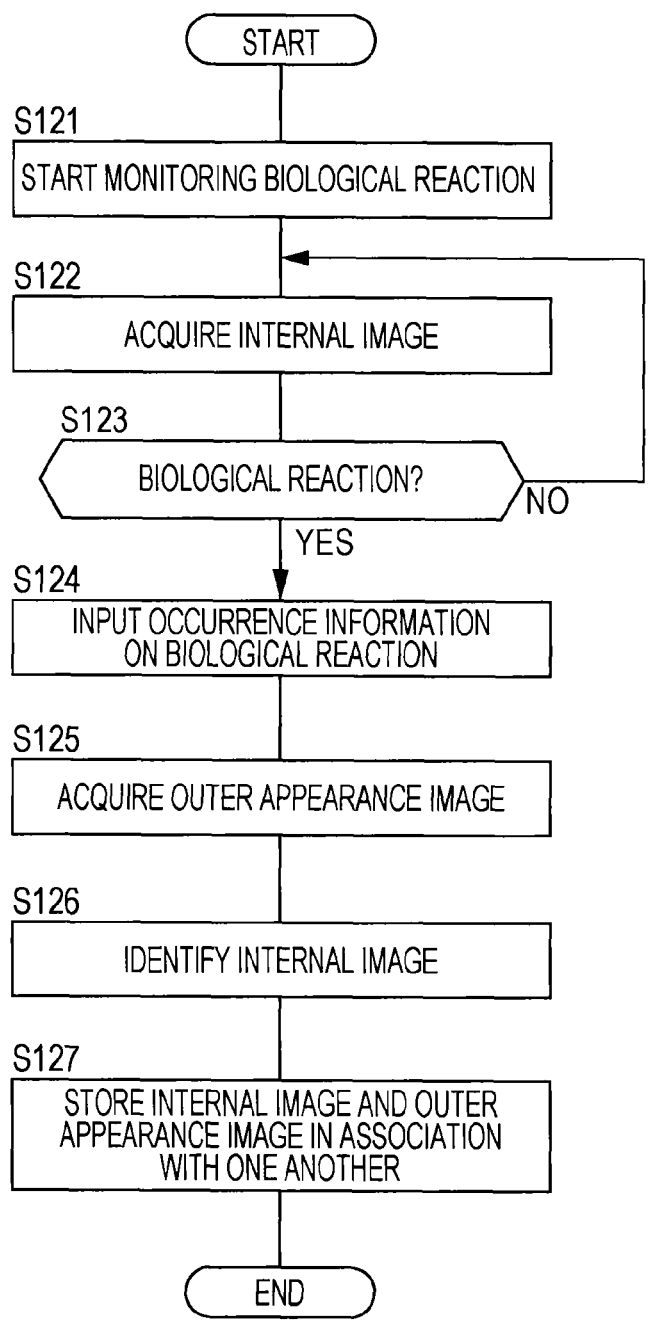
FIG. 16 is a flowchart illustrating an operation of the medical image diagnostic apparatus according to the first modified example.

An operation of the medical image diagnostic apparatus according to this modified example is described. FIG. 16 illustrates an example of the operation.

(S121: Start Monitoring Biological Reaction)
The sensor unit 200 starts monitor (monitoring) of the biological reaction.

(S122: Acquire Internal Image)
In the same manner as the above-mentioned embodiments, the acquisition of the plurality of internal images different in time phase is started.

(S123 and S124: Input Occurrence Information on Biological Reaction)
When sensing the occurrence of a predetermined biological reaction (S123: YES), the sensor unit 200 inputs the signal serving as the occurrence information on the biological reaction to the control unit 41 (S124).

(S125: Acquire Outer Appearance Image)
The control unit 41 that has received the input of the occurrence information on the biological reaction controls the outer appearance image acquiring unit 50 to photograph the predetermined body part of the subject E. Alternatively, the control unit 41 that has received the input of the occurrence information on the biological reaction causes predetermined alarm information to be output. The operator who has recognized the alarm information operates the operation unit 46 to instruct the acquisition of the outer appearance image. In response to the instruction, the outer appearance image acquiring unit 50 performs the photographing. Therefore, the outer appearance image is obtained.

(S126: Identify Internal Image)
The image identifying unit 434 executes any one of the above-mentioned processings, to thereby identify the internal image acquired at substantially the same time as the input of the occurrence information on the biological reaction (S124) among the plurality of internal images acquired in Step S122.

(S127: Store Internal Image and Outer Appearance Image in Association with Each Another)
The control unit 41 stores the internal image identified in Step S126 and the outer appearance image acquired in Step S125 in the storage unit 44 in association with each another. This is the end of the operation relating to this operation example.

Figure 17:
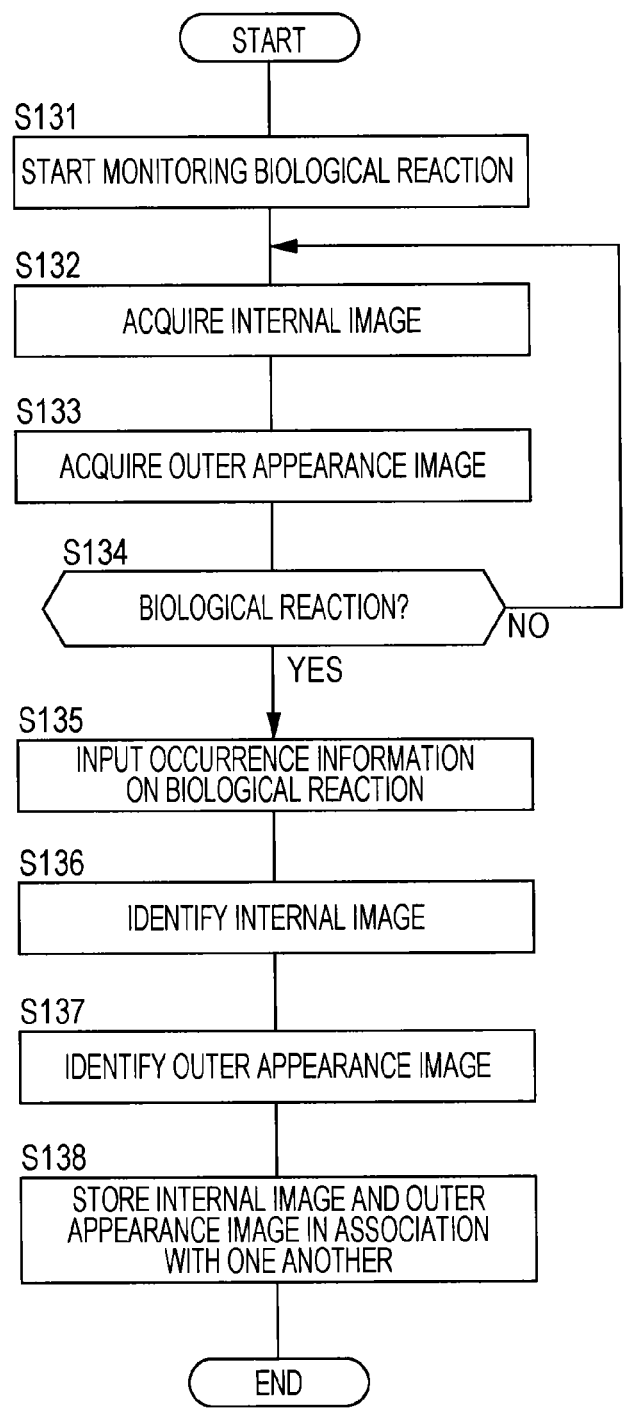
FIG. 17 is a flowchart illustrating another operation of the medical image diagnostic apparatus according to the first modified example.

Another operation example is described with reference to FIG. 17.

(S131: Start Monitoring Biological Reaction)
The sensor unit 200 starts monitor (monitoring) of the biological reaction.

(S132: Acquire Internal Image)
In the same manner as the above-mentioned embodiments, the acquisition of the plurality of internal images different in time phase is started.

(S133: Acquire Outer Appearance Image)
The outer appearance image acquiring unit 50 starts the moving image photographing for the predetermined body part of the subject E. Accordingly, the plurality of outer appearance images along time series are obtained. The acquisition of the outer appearance image is continued until at least the input of the occurrence information on the biological reaction (S134).

(S134 and S135: Input Occurrence Information on Biological Reaction)
When sensing the occurrence of the predetermined biological reaction (S134: YES), the sensor unit 200 inputs the signal serving as the occurrence information on the biological reaction to the control unit 41 (S135).

(S136: Identify Internal Image)
The image identifying unit 434 identifies the internal image acquired at substantially the same time as the input of the occurrence information on the biological reaction (S135) among the plurality of internal images acquired in Step S132.

(S137: Identify Outer Appearance Image)
In addition, the image identifying unit 434 identifies the outer appearance image acquired at substantially the same time as the input of the occurrence information on the biological reaction (S135) among the plurality of outer appearance images acquired in Step S133. Note that, the processing for identifying the internal image and the processing for identifying the outer appearance image may be performed in any order or may be performed in parallel.

(S138: Store Internal Image and Outer Appearance Image in Association with Each Another)
The control unit 41 stores the internal image identified in Step S136 and the outer appearance image identified in Step S137 in the storage unit 44 in association with each another. This is the end of the operation relating to this operation example.

According to the medical image diagnostic apparatus according to this modified example, in the same manner as the above-mentioned embodiments, it is possible to grasp the relationship between the action state of the body and the occurrence timing of the biological reaction. In addition, the occurrence of the biological reaction can be automatically sensed, which does not bother the user.

Second Modified Example

Figure 18:
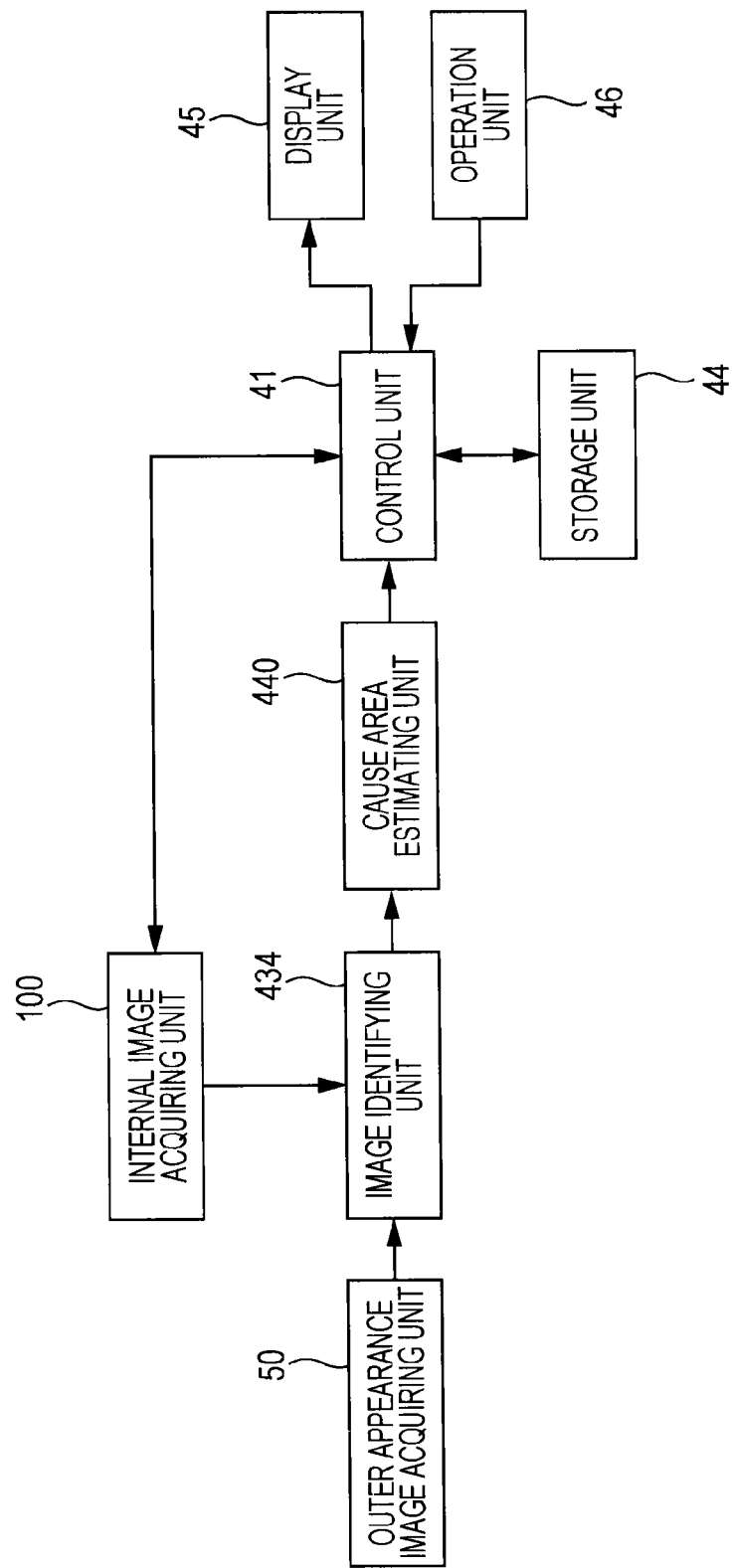
FIG. 18 is a block diagram illustrating a configuration of a medical image diagnostic apparatus according to a second modified example.

In a second modified example, a function of estimating and presenting the body part causing the pain is described. FIG. 18 illustrates a configuration example of a medical image diagnostic apparatus according to this modified example. The medical image diagnostic apparatus according to this modified example is obtained by, for example, adding a cause area estimating unit 440 to the processing unit 43 of the X-ray CT apparatus 1 according to the above-mentioned embodiments.

The cause area estimating unit 440 analyzes at least one internal image including the internal image identified by the image identifying unit 434, and estimates a cause area for the pain. In addition, the cause area estimating unit 440 may be configured to analyze an internal area of the cause area and estimate a degree of the pain. The cause area estimating unit 440 is an example of an "estimating unit".

The description is made by taking the examination of the joint part as an example. The cause area estimating unit 440 analyzes the internal image as illustrated in FIG. 3, and identifies the image area (bone area) corresponding to the bones located in the joint part. In addition, the cause area estimating unit 440 analyzes the identified bone area, and estimates the cause area for the pain based on the shape or pixel value (such as brightness value or CT value) of the bone area. At this time, a result of another examination performed in advance may be taken into consideration. Further, information previously created based on clinical data by associating at least one of the shape and the pixel value with the cause area may be referred to. The cause area for the pain includes the image area corresponding to an area of pathology such as cartilage abrasion, fracture, and a tumor.

Further, the cause area estimating unit 440 analyzes the internal image with a focus on the estimated cause area, and estimates the degree of the pain based on the shape or the pixel value (such as brightness value or CT value) of the cause area. At this time, the result of another examination performed in advance may be taken into consideration. Further, information previously created based on the clinical data by associating at least one of the shape, size, and pixel value of the cause area with the degree of the pain may be referred to.

When displaying the internal image on the display unit 45, the control unit 41 causes the display mode for the cause area to become different from the display mode for another image area. As a specific example thereof, the cause area can be displayed by being colored or framed. Alternatively, the control unit 41 can display the cause area in the display mode corresponding to the estimated degree of the pain. As a specific example thereof, depending on the degree of the pain, the cause area can be displayed by changing a display color thereof or changing a display color of a frame and a form of a line thereof (such as solid line or broken line).

Figure 19:
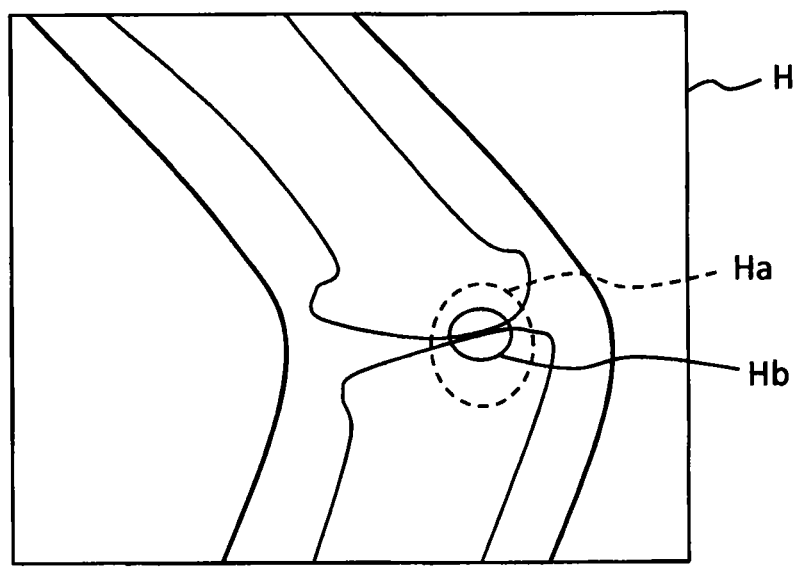
FIG. 19 illustrates a display mode employed by the medical image diagnostic apparatus according to the second modified example.

FIG. 19 illustrates an example of the display mode of the internal image according to this modified example. In an internal image H, a frame Ha indicating the cause area for the pain estimated by the cause area estimating unit 440 is displayed as a broken line. In addition, a frame Hb indicating the area estimated to have a particularly large degree of the pain within the cause area is displayed as a solid line.

According to such modified example, in addition to the effects of the above-mentioned embodiments and the above-mentioned modified example, it is possible to easily grasp the body part causing the pain as well as the degree of the pain.

Third Modified Example

Figure 20:
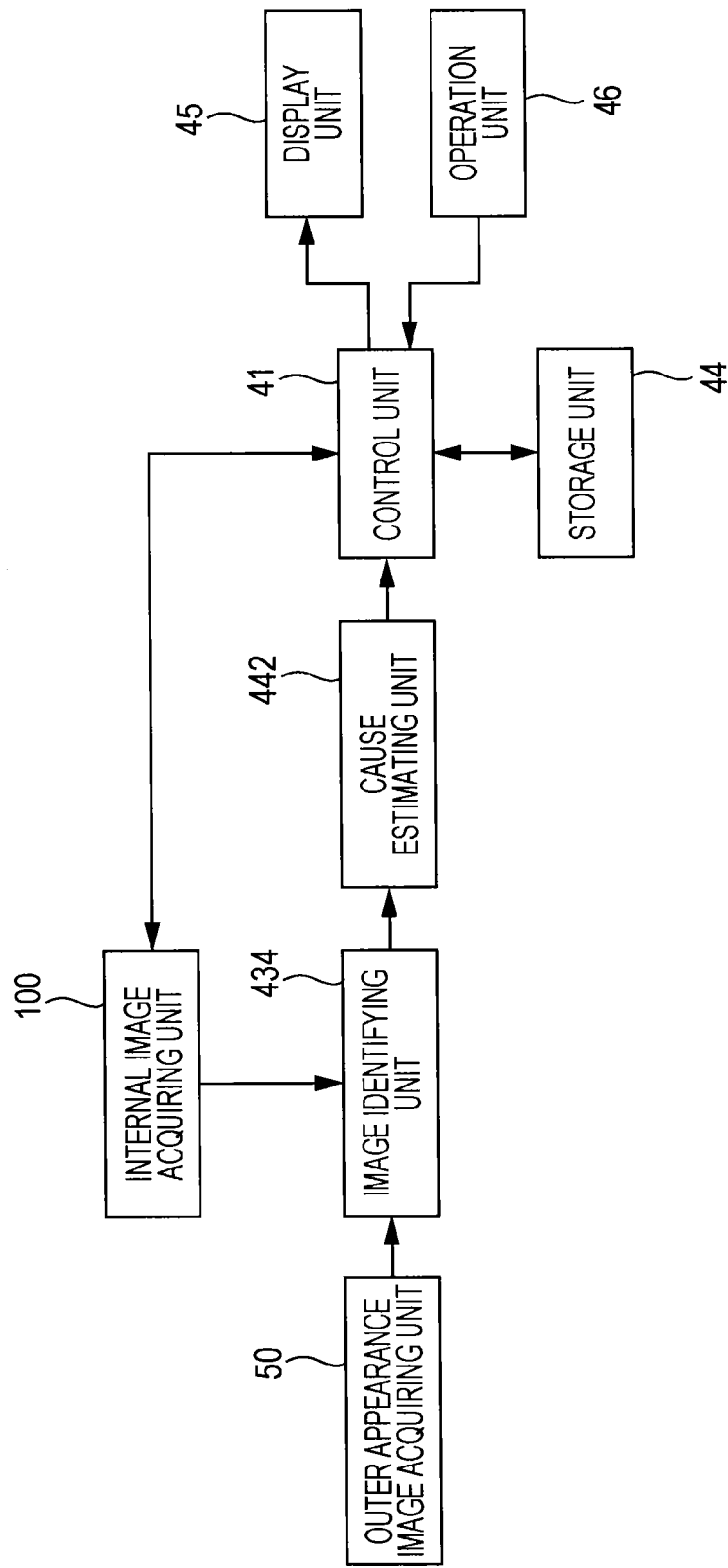
FIG. 20 is a block diagram illustrating a configuration of a medical image diagnostic apparatus according to a third modified example.

In a third modified example, a function of estimating and presenting the cause of the pain is described. FIG. 20 illustrates a configuration example of a medical image diagnostic apparatus according to this modified example. The medical image diagnostic apparatus according to this modified example is obtained by, for example, adding a cause estimating unit 442 to the processing unit 43 of the X-ray CT apparatus 1 according to the above-mentioned embodiments. This modified example can be used by being combined with the second modified example.

The cause estimating unit 442 analyzes at least one internal image including the internal image identified by the image identifying unit 434, and estimates the cause of the pain. The cause estimating unit 442 is an example of the "estimating unit".

The description is made by taking the examination of the joint part as an example. In this case, examples of the cause of the pain include the cartilage abrasion, the fracture, and the tumor. The cause estimating unit 442 analyzes the internal image as illustrated in FIG. 3, and identifies the image area (bone area) corresponding to the bones located in the joint part. In addition, the cause estimating unit 442 analyzes the identified bone area, and estimates the cause of the pain based on the shape or pixel value (such as brightness value or CT value) of the bone area. At this time, the result of another examination performed in advance may be taken into consideration. Further, the information previously created based on the clinical data by associating at least one of the shape and the pixel value with the cause area may be referred to.

Figure 21:
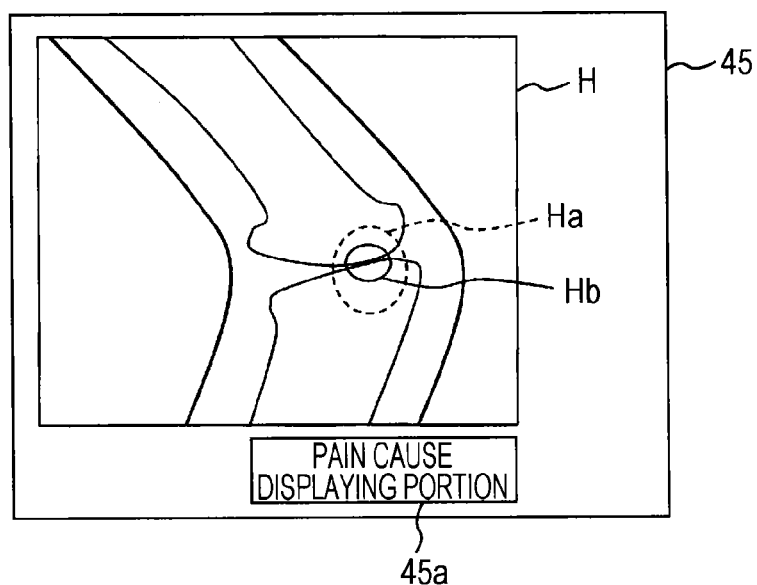
FIG. 21 illustrates a display mode employed by the medical image diagnostic apparatus according to the third modified example.

The control unit 41 displays the information indicating the cause of the pain estimated by the cause estimating unit 442 on the display unit 45. The information is, for example, text information (such as "cartilage abrasion", "fracture", or "tumor") indicating the cause of the pain. FIG. 21 illustrates a specific example thereof. The display unit 45 includes a pain cause displaying portion 45a. The control unit 41 displays the text information "cartilage abrasion" indicating the cause of the pain estimated by the cause estimating unit 442 in the pain cause displaying portion 45a.

According to this modified example, in addition to the effects of the above-mentioned embodiments and the above-mentioned modified examples, it is possible to easily grasp the cause of the pain.

Other Modified Example

The medical image diagnostic apparatus according to the embodiments or the modified examples (first medical image diagnostic apparatus) can transmit the timing information and at least one of the internal image and the outer appearance image to another medical image diagnostic apparatus (second medical image diagnostic apparatus).

The second medical image diagnostic apparatus may employ a modality of an arbitrary type such as the X-ray CT apparatus, the X-ray machine, a magnetic resonance imaging (MRI) apparatus, a positron emission tomography (PET) apparatus, a single photon emission computed tomography (SPECT) apparatus, and an ultrasonography apparatus.

The second medical image diagnostic apparatus acquires the occurrence timing of the biological reaction based on the information received from the first medical image diagnostic apparatus, and performs the photographing based on the occurrence timing. Accordingly, also on another medical image diagnostic apparatus, the photographing can be performed at the timing corresponding to the occurrence of the biological reaction. Further, it is possible to grasp the relationship between the action state of the body and the occurrence timing of the biological reaction.

By superimposing at least one of the internal image and the outer appearance image obtained by the first medical image diagnostic apparatus on the image acquired by the second medical image diagnostic apparatus, the second medical image diagnostic apparatus can display a fusion image thereof. A publicly-known method can be used as fusion image displaying processing including processing for positioning the images.

The timing information and at least one of the internal image and the outer appearance image acquired by the medical image diagnostic apparatus according to the embodiments or the modified examples can be used for medical practice other than medical image diagnosis. Application examples thereof include design of an artificial joint, rehabilitation, and informed consent.

In the design of the artificial joint, reference can be made to the timing at which the pain occurs and to a moveable range of the joint that can be grasped based on the plurality of internal images. The rehabilitation can be carried out while grasping how much the joint is bent when the pain occurs (to which extent). In the informed consent, a comprehensible explanation can be given of the relationship between the action state of the body and the occurrence timing of the biological reaction.

In each of the above-mentioned embodiments and modified examples, the example of the X-ray CT apparatus is described in detail, but the same configuration can be applied to the X-ray machine. The X-ray machine outputs X-rays from the X-ray tube, and detects and visualizes the X-rays that have passed through the subject by using the X-ray detector (imaging plate), to thereby acquire the internal image. The X-ray machine not only forms an image along a plane orthogonal to a direction that connects between the X-ray tube and the X-ray detector but also restructures a three-dimensional image from a plurality of images photographed from different directions. The X-ray machine is used as the "internal image acquiring unit".

A medical image diagnostic apparatus according to another embodiment is described. This embodiment includes an internal image acquiring unit, an outer appearance image acquiring unit, a storage unit, and a control unit. The internal image acquiring unit continuously or intermittently irradiates the predetermined body part of the subject with X-rays to acquire the plurality of internal images different in time phase. The outer appearance image acquiring unit acquires the outer appearance image by photographing the predetermined body part at least at the photographing timing corresponding to the occurrence of a predetermined biological reaction of the subject. The control unit stores the plurality of internal images and the outer appearance image in the storage unit in association with each other. Here, the storage unit does not necessarily store all the internal images or all the outer appearance images that have been acquired as described above.

An example of this medical image diagnostic apparatus is described. An acquisition operation for the internal image performed by the internal image acquiring unit is synchronized with an acquisition operation for the outer appearance image performed by the outer appearance image acquiring unit. As an example of this synchronization, both image acquiring units can start image acquiring operations of at the same time. Further, one of the image acquiring operations can be started after the other image acquiring operation is started. In those examples, timings of both the image acquiring operations can be grasped in terms of the same time axis. For example, both the image acquiring operations (for example, timing at which image acquisition is started) can be configured to be recorded as coordinates on the same time axis. Further, both the image acquiring operations can be configured to have a time difference therebetween (for example, time difference therebetween in the timing to start the image acquisition; including a time difference of zero) recorded. Such time-related processing can be performed by using, for example, a timing function provided to the control unit (microprocessor).

The control unit performs such synchronization control, and stores the internal image and the outer appearance image acquired thereby in the storage unit in association with each other. At this time, the control unit can store time-related information such as coordinate values in the time axis and the time difference described above in the storage unit in association with the internal image and the outer appearance image. Further, in a case of performing both the image acquiring operations with constantly the same time difference or other such case, there is no need to store the time-related information.

When both the images are viewed, the display timings for both the images can be controlled in consideration of the stored time-related information, a predetermined time difference, or the like. In other words, the display timings for both the images can be controlled by performing the same synchronization control as the acquisition timings for those images. Accordingly, the time axes of both the images being displayed can be caused to coincide with each other (in other words, both the images can be displayed along the same time axis).

According to such an embodiment, for example, while grasping the action state of the body based on one of the images, it is possible to grasp the occurrence timing of the biological reaction based on the other image. Therefore, it is possible to obtain the relationship between the action state of the body and the occurrence timing of the biological reaction.

It is possible to use the medical image diagnostic apparatus according to the embodiments and the modified examples in the following manner. First, while instructing an examinee to bend and stretch the joint, without administering anesthesia thereto, first photographing is performed to acquire the image in the time phase corresponding to the occurrence timing of the pain. This image may be the internal image or the outer appearance image. Second photographing is performed by administering anesthesia to the examinee, which (almost) keeps the examinee from feeling the pain. In the second photographing, it is possible to grasp the bent state of the joint by comparing the image obtained by the first photographing with a newly-acquired image. Therefore, it is possible to perform the photographing while maintaining the bent state causing the pain and to perform the photographing while instructing the examinee to gradually bend and stretch the joint. Accordingly, the state of the joint causing the pain can be examined in detail.

Further, in a case where the same body part of the subject is examined a plurality of times as in preoperative/postoperative observations and follow-ups, the image at the occurrence timing of the biological reaction obtained in the past can be acquired by using the image in the time phase corresponding to the occurrence timing for the current examination. Accordingly, a change in the state of an affected area can be grasped in detail. In addition, a relationship between the change in the state of the affected area and the biological reaction can also be grasped in detail.

While certain embodiments have been described, these embodiments have been presented by way of example only, and are not intended to limit the scope of the inventions. Indeed, the novel systems described herein may be embodied in a variety of their forms; furthermore, various omissions, substitutions and changes in the form of the systems described herein may be made without departing from the spirit of the inventions. The accompanying claims and their equivalents are intended to cover such forms or modifications as would fall within the scope and spirit of the inventions.

What is claimed is:

1. A medical image diagnostic apparatus, comprising:
an internal image acquiring unit configured to irradiate a body part of a subject with X-rays to acquire a plurality of internal images different in time phase;
an outer appearance image acquiring unit configured to acquire an outer appearance image by photographing the body part of the subject;
an analysis unit configured to analyze the outer appearance image to acquire first shape information indicating a shape of the body part of the subject and to analyze each of the plurality of internal images to acquire second shape information indicating a shape of the body part of the subject;

a display control unit configured to display the outer appearance image and the internal image by superimposing one on another so that the body part of the subject included in the outer appearance image and the body part of the subject included in the internal image are located in the same position based on the first shape information and the second shape information;

an input unit configured to input occurrence information indicating an occurrence of a biological reaction of the subject; and an identification unit configured to identify the internal image acquired at substantially the same time as inputting of the occurrence information among the plurality of internal images, wherein:

the outer appearance image acquiring unit is configured to photograph the body part of the subject at a photographing timing corresponding to the inputting of the occurrence information to acquire the outer appearance image, and the display control unit is configured to display the outer appearance image acquired at the photographing timing and the internal image identified by the identification unit in association with each other.

2. A medical image diagnostic apparatus according to claim 1, wherein the identification unit is configured to identify the internal image corresponding to, among a plurality of pieces of the second shape information that have been acquired, one of the plurality of pieces of second shape information that substantially matches the first shape information.

3. A medical image diagnostic apparatus according to claim 1, wherein the first shape information and the second shape information each comprise contour information indicating a shape of a contour of a body surface of the body part of the subject.

4. A medical image diagnostic apparatus according to claim 1, wherein:

the body part of the subject comprises a joint part; and the first shape information and the second shape information each comprise angle information indicating an angle in the joint part formed between bones.

5. A medical image diagnostic apparatus according to claim 1, wherein:

the analysis unit is configured to analyze the outer appearance image to acquire first feature position information indicating a position of a feature area within the outer appearance image, and to analyze each of the plurality of internal images to acquire second feature position information indicating a position of the feature area within the each of the plurality of internal images; and the identification unit is configured to identify the internal image based on the first feature position information and a plurality of pieces of the second feature position information that have been acquired.

6. A medical image diagnostic apparatus according to claim 5, wherein the first feature position information and the second feature position information each comprise marker position information indicating a position of an image area representing a marker attached to a body surface of the subject.

7. A medical image diagnostic apparatus according to claim 1, wherein the identification unit is configured to:

receive first timing information indicating a timing at which the occurrence information is input by the input unit and second timing information indicating a timing at which each of the plurality of internal images is acquired by the internal image acquiring unit; and identify one of the plurality of internal images corresponding to the second timing information received at substantially the same time as the first timing information.

8. A medical image diagnostic apparatus according to claim 1, wherein:

the outer appearance image acquiring unit is configured to repeatedly photograph the body part of the subject to sequentially acquire the outer appearance images; and the identification unit is configured to identify the outer appearance image acquired at substantially the same time as inputting of the occurrence information among the sequentially-acquired outer appearance images.

9. A medical image diagnostic apparatus according to claim 1, wherein the input unit comprises a sensor unit configured to monitor a state of the subject, and to sense an occurrence of a biological reaction of the subject, to input a signal serving as the occurrence information.

10. A medical image diagnostic apparatus according to claim 9, wherein the sensor unit is configured to sense a change in biological information accompanied by pain as the biological reaction.

11. A medical image diagnostic apparatus according to claim 1, further comprising an instruction unit configured to issue an instruction to display one image of the internal image and the outer appearance image that are associated with each other, wherein the display control unit is configured to display the one image and another image on a display unit in response to the instruction to display the one image.

12. A medical image diagnostic apparatus according to claim 1, wherein the display control unit is configured to display a moving image based on the plurality of internal images acquired by the internal image acquiring unit, and to display information indicating an occurrence of a biological reaction of the subject at a timing at which the internal image identified by the identification unit is displayed.

13. A medical image diagnostic apparatus according to claim 1, further comprising an estimating unit configured to analyze at least one internal image comprising the internal image identified by the identification unit to estimate a cause area for pain, wherein the display control unit is configured to display the internal image by distinguishing a display mode for the estimated cause area for the pain from a display mode for another image area.

14. A medical image diagnostic apparatus according to claim 13, wherein:

the estimating unit is configured to analyze the at least one internal area to estimate a degree of the pain; and the display control unit is configured to display the cause area for the pain in a display mode corresponding to the estimated degree of the pain.

15. A medical image diagnostic apparatus according to claim 1, further comprising an estimating unit configured to analyze at least one internal image comprising the internal images identified by the identification unit to estimate a cause of pain, wherein the display control unit is configured to display information indicating the estimated cause of the pain.

16. A medical image diagnostic apparatus according to claim 1, wherein the internal image acquiring unit comprises one of:

an X-ray CT apparatus for repeatedly scanning the subject by using X-rays to collect data, and restructuring the collected data to form the plurality of internal images; and an X-ray machine for performing one of continuous application of X-rays and intermittent application of X-rays to the subject, detecting the X-rays that have passed through the subject, and forming the plurality of internal images along a plane substantially orthogonal to an application direction of the X-rays.

17. A medical image diagnostic apparatus according to claim 1, further comprising a storage unit that stores the outer appearance image acquired by the outer appearance image acquiring unit and timing information indicating a timing at which the occurrence information is input,
wherein the internal image acquiring unit is configured to acquire a new internal image based on the outer appearance image and the timing information.

18. A medical image diagnostic apparatus according to claim 17, wherein the internal image acquiring unit is configured to acquire the new internal image based on the outer appearance image and the timing information in a specific time phase corresponding to the timing information.

19. A medical image diagnostic apparatus according to claim 18, wherein the internal image acquiring unit is configured to acquire a plurality of the new internal images by applying X-rays having a first intensity in the specific time phase and applying X-rays having a second intensity that is lower than the first intensity in a time phase other than the specific time phase.

20. A medical image diagnostic apparatus according to claim 19, further comprising a time phase sensing unit configured to sense arrival of the specific time phase by comparing the new internal image or a new outer appearance image acquired by the outer appearance image acquiring unit with the outer appearance image stored in the storage unit, the new internal images being acquired by applying the X-rays having the second intensity,
wherein the internal image acquiring unit is configured to switch an X-ray intensity from the second intensity to the first intensity in response to sensing arrival of the specific time phase.

21. A medical image diagnostic apparatus according to claim 17, wherein the internal image acquiring unit is configured to acquire the new internal image in a time phase period based on the outer appearance image and the timing information, the time phase period comprising a time phase corresponding to the timing information.

22. A medical image diagnostic apparatus according to claim 21, wherein the internal image acquiring unit is configured to acquire a plurality of the new internal images by applying X-rays having a first intensity in the time phase comprised in the time phase period and applying X-rays having a second intensity that is lower than the first intensity in a time phase other than the time phase period.

23. A medical image diagnostic apparatus according to claim 22, further comprising a time phase sensing unit configured to sense arrival of the time phase included in the time phase period by comparing the new internal image acquired by applying the X-rays having the second intensity or a new outer appearance image acquired by the outer appearance image acquiring unit with the stored outer appearance image,
wherein the internal image acquiring unit is configured to switch an X-ray intensity from the second intensity to the first intensity in response to sensing the arrival of the time phase comprised in the time phase period.

24. A medical image diagnostic apparatus according to claim 20 or 23, wherein:
the time phase sensing unit comprises:
a generation unit configured to respectively analyze the new internal image acquired by applying the X-rays having the second intensity or the new outer appearance image and the outer appearance image stored in the storage unit, to generate body part shape information on the subject indicating the shape of the body part of the subject; and
a determination unit configured to determine whether or not the body part shape information on the subject generated from the new internal image or the new outer appearance image and the body part shape information on the subject generated from the outer appearance image stored in the storage unit substantially match each other; and
the time phase sensing unit is configured to determine arrival of the time phase when the body part shape information on the subject generated from the new internal image or the new outer appearance image is substantially matched with the body part shape information on the subject generated from the outer appearance image stored in the storage unit.

25. A medical image diagnostic apparatus according to claim 17, wherein the display control unit is configured to display a moving image based on the plurality of internal images acquired by the internal image acquiring unit, and to display information indicating an occurrence timing of a biological reaction of the subject based on the timing information.

* * * * *